(12) United States Patent
Wallner et al.

(10) Patent No.: US 6,890,904 B1
(45) Date of Patent: May 10, 2005

(54) ANTI-TUMOR AGENTS

(75) Inventors: Barbara P. Wallner, Cohasset, MA (US); Glenn Miller, Merrimac, MA (US)

(73) Assignee: Point Therapeutics, Inc., Boston, MA (US)

( * ) Notice: Subject to any disclaimer, the term of this patent is extended or adjusted under 35 U.S.C. 154(b) by 0 days.

(21) Appl. No.: 09/578,363

(22) Filed: May 25, 2000

Related U.S. Application Data

(60) Provisional application No. 60/135,861, filed on May 25, 1999.

(51) Int. Cl.[7] .................... A61K 38/05; A61K 38/06; A61K 38/07; A61K 38/08; A61K 38/10

(52) U.S. Cl. ..................... 514/14; 514/15; 514/16; 514/17; 514/18; 514/19

(58) Field of Search ................ 514/2, 13, 14, 514/15, 16, 17, 18, 19, 20

(56) References Cited

U.S. PATENT DOCUMENTS

| | | | |
|---|---|---|---|
| 4,318,904 A | 3/1982 | Shaw et al. | 424/177 |
| 4,443,609 A | 4/1984 | Oude Alink et al. | 548/111 |
| 4,499,082 A | 2/1985 | Shenvi et al. | 514/2 |
| 4,582,821 A | 4/1986 | Kettner et al. | 514/18 |
| 4,636,492 A | 1/1987 | Kettner et al. | 514/18 |
| 4,644,055 A | 2/1987 | Kettner et al. | 530/330 |
| 4,652,552 A | 3/1987 | Kettner et al. | 514/18 |
| 4,935,493 A | 6/1990 | Bachovchin et al. | 530/331 |
| 4,963,655 A | 10/1990 | Kinder et al. | 530/331 |
| 5,093,477 A | 3/1992 | Mölling et al. | 530/328 |
| 5,187,157 A | 2/1993 | Kettner et al. | 514/18 |
| 5,215,926 A | 6/1993 | Etchells, III et al. | 436/501 |
| 5,242,904 A | 9/1993 | Kettner et al. | 514/18 |
| 5,250,720 A | 10/1993 | Kettner et al. | 558/288 |
| 5,288,707 A | 2/1994 | Metternich | 514/19 |

(Continued)

FOREIGN PATENT DOCUMENTS

| | | | |
|---|---|---|---|
| AU | 729369 | * | 2/2001 |
| DE | 158109 | | 12/1982 |
| DE | 270382 A1 | | 7/1989 |
| DE | 296075 A5 | | 11/1991 |
| EP | 0356223 A2 | | 2/1990 |

(Continued)

OTHER PUBLICATIONS

Thompson, R.C.., "Peptide Aldehydes:Potent Inhibitors of Serine and Cysteine Proteases" *Methods In Enzymology*, vol. XLVI, Chapter 19 pp. 220–225 (not dated).

Cordes, E., et al., "Transition States For Hydrolysis Of Acetals, Ketals Glycosides, And Glycosylamines", Chapter 11, pp. 429–465 (not dated).

Baugh, R., et al., "Role and Potential Therapeutic Value of Proteinase Inhibitors in Tissue Destruction" *Proteinases And Tumor Invasion*, (1980), 165:157–179.

(Continued)

*Primary Examiner*—Jeffrey Edwin Russel
(74) *Attorney, Agent, or Firm*—Wolf, Greenfield & Sacks, P.C.

(57) ABSTRACT

A method for treating subjects with abnormal cell proliferation is provided. The method involves administering to subjects in need of such treatment an effective amount of an agent of Formula I, to inhibit cell proliferation such as that associated with tumor growth and metastasis. A method for inhibiting angiogenesis in an abnormal proliferative cell mass by the administration of an agent of Formula I is also provided.

64 Claims, 5 Drawing Sheets

U.S. PATENT DOCUMENTS

| | | | |
|---|---|---|---|
| 5,296,604 A | 3/1994 | Hanko et al. | 546/169 |
| 5,329,028 A | 7/1994 | Ashkenazi et al. | 548/548 |
| 5,378,624 A | 1/1995 | Berenson et al. | 435/239 |
| 5,384,410 A | 1/1995 | Kettner | 548/405 |
| 5,444,049 A | 8/1995 | de Nanteuil et al. | 514/18 |
| 5,462,928 A | 10/1995 | Bachovchin et al. | 514/19 |
| 5,506,130 A | 4/1996 | Peterson et al. | 435/240.1 |
| 5,527,923 A | 6/1996 | Klingler et al. | 548/570 |
| 5,543,396 A | 8/1996 | Powers et al. | 514/19 |
| 5,554,728 A | 9/1996 | Basava et al. | 530/327 |
| 5,587,299 A | 12/1996 | Rettig et al. | 435/69.1 |
| 5,635,386 A | 6/1997 | Palsson et al. | 435/372 |
| 5,635,387 A | 6/1997 | Fei et al. | 435/378 |
| 5,639,725 A | 6/1997 | O'Reilly et al. | 514/12 |
| 5,646,043 A | 7/1997 | Emerson et al. | 435/373 |
| 5,753,230 A * | 5/1998 | Brooks et al. | 424/158.1 |
| 5,767,242 A | 6/1998 | Zimmermann et al. | 530/350 |
| 5,854,205 A * | 12/1998 | O'Reilly et al. | 514/2 |
| 5,854,221 A | 12/1998 | Cao et al. | 514/12 |
| 5,965,373 A | 10/1999 | Zimmermann et al. | 435/7.1 |
| 5,965,532 A * | 10/1999 | Bachovchin | 514/12 |
| 6,040,145 A | 3/2000 | Huber et al. | 435/7.2 |
| 6,090,786 A | 7/2000 | Augustyns et al. | 514/19 |
| 6,265,551 B1 | 7/2001 | Duke-Cohan et al. | 530/389.6 |
| 6,503,882 B2 | 1/2003 | Huber et al. | 514/2 |
| 2002/0034789 A1 | 3/2002 | Zimmermann et al. | 435/69.7 |
| 2003/0130199 A1 | 7/2003 | von Hoersten et al. | |

FOREIGN PATENT DOCUMENTS

| | | | |
|---|---|---|---|
| EP | 0371467 A2 | 6/1990 | |
| EP | 0471651 A2 | 2/1992 | |
| EP | 0481311 A2 | 4/1992 | |
| EP | 0615978 A1 | 9/1994 | |
| EP | 0420913 B1 | 11/1995 | |
| EP | 0688788 A1 | 12/1995 | |
| NZ | 335543 | * | 3/2001 |
| WO | WO89/03223 | 4/1989 | |
| WO | WO91/16339 | 10/1991 | |
| WO | WO91/17767 | 11/1991 | |
| WO | WO92/12140 | 7/1992 | |
| WO | WO92/17490 | 10/1992 | |
| WO | WO93/02057 | 2/1993 | |
| WO | WO93/05011 | 3/1993 | |
| WO | WO93/08259 | 4/1993 | |
| WO | WO93/10127 | 5/1993 | |
| WO | WO93/16102 | 8/1993 | |
| WO | WO94/03055 | 2/1994 | |
| WO | WO94/09132 | 4/1994 | |
| WO | WO94/20526 | 9/1994 | |
| WO | WO94/25873 | 11/1994 | |
| WO | WO94/28915 | 12/1994 | |
| WO | WO94/29335 | 12/1994 | |
| WO | WO95/11689 | 5/1995 | |
| WO | WO95/12618 | 5/1995 | |
| WO | WO 95/15309 | 6/1995 | |
| WO | WO95/29190 | 11/1995 | |
| WO | WO 95/29233 | 11/1995 | |
| WO | WO95/29691 | 11/1995 | |
| WO | WO95/34538 | 12/1995 | |
| WO | WO96/40263 | 12/1996 | |
| WO | WO96/40858 | 12/1996 | |
| WO | WO 97/34927 | 9/1997 | |
| WO | WO98/00439 | 1/1998 | |
| WO | WO 98/25644 | 6/1998 | |
| WO | WO98/50046 | 11/1998 | |
| WO | WO98/50066 | 11/1998 | |
| WO | WO99/19864 | 4/1999 | |
| WO | WO 99/47152 A2 | 9/1999 | |
| WO | WO 99/56753 A1 | 11/1999 | |
| WO | WO 99/62914 | 12/1999 | |
| WO | WO 00/10549 | 3/2000 | |

OTHER PUBLICATIONS

Bodanszky, M., "Principles Of Peptide Synthesis", *Springer–Verlag*, (1984), vol. 16.

Bodanszky, M., "The Practice Of Peptide Synthesis", *Springer–Verlag*, (1984), vol. 21.

Matteson, D., et al., "Synthesis And Properties Of Pinanediol α–Amido Boronic Esters" *Organometallics*, (1984), 3:1284–1288.

Powers, J.C. and Bengali, Z.H., "Elastase Inhibitors for Treatment of Emphysema" *NHLBI Workshop Summary US Dept. of Health and Human Services*, (1985), 1097–1100.

Yoshimoto, T., et al., "Comparison Of Inhibitory Effects Of Prolinal–Containing Peptide Derivates On Prolyl . . . ", *J. Biochemistry* (1985), 98:975–979.

Kettner, C.A., et al., "Kinetic Properties Of The Binding Of Alpha–Lytic Protease To Peptide Boronic Acids", *Biochemistry*, (1988), 27:7682–7688.

Tam, J.P., "Synthetic Peptide Vaccine Design: Synthesis And Properties Of A High–Density Multiple Antigenic Peptide System", *Proc Natl Acad Sci U S A*, (1988), 85:5409–5413.

Bailey, P.D., "An Introduction To Peptide Chemistry", *Wiley Publishers*, (1990), 1–81.

Kettner, C.A. and Shenvi, A.B., "Peptide boronic acid inhibitors of trypsin–like proteases, their preparation and use as anticoagulants and inlammation Inhibitors" *Chemical Abstracts*, (1990), 112:80 (91790c).

Bachovchin, W.W., et al., "Inhibition Of Igal Proteinases From Neisseria Gonorrhoeae And Hemophilus Hemophilus Influenzae By Peptide Prolyl Boronic Acids", *J Biol Chem*, (1990), 265: 3738–3743.

Kinder D.H., et al., "Analogues Of Carbamyl Aspartate As Inhibitors Of Dihydroorotase: Preparation Of Boronic Acid Transition–State Analogues And A Zinc Chelator Carbamylhomocysteine", *J Med Chem*, (1990), 33:819–823.

Flentke, G.R., et al., "Inhibition Of Dipeptidyl Aminopeptidase Iv (Dp–Iv) By Xaa–Boropro Dipeptides And Use Of These Inhibitors To Examine The Role Of Dp–Iv In T–Cel Function" *Proc Natl Acad Sci U S A*, (1991), 88:1556–1559.

Schon, E., et al., "Dipeptidyl Peptidase IV In The Immune System. Effects Of Specific Enzyme Inhibitors On On Activity Of Dipeptidase IV And Proliferation Of Human Lymphocytes", *Biological Chemistry Hoppe Seyler* 372:305–311 (1991).

Kubota, T., et al., "Involvement Of Dipeptidyl Peptidase Iv In An In Vivo Immune Response", *Clin Exp Immunol*, (1992), 89:192–197.

Gutheil, W.G., et al., "Separation Of L–Pro–DL–Boropro Into Its Component Diastereomers And Kinetic Analysis Of Their Inhibition Of Dipeptidyl Peptidase IV. A New Method For The Analysis Of Slow, Tight–Binding Inhibitition", *Biochemistry*, (1993), 32:8723–8731.

Kelly, T.A., et al., "Immunosuppressive Boronic Acid Dipeptides: Correlation Between Conformation And Activity", *J Am Chem Soc*, (1993), 115:12637–12638.

Songyang, Z., et al., "SH2 Domains Recognize Specific Phosphopeptide Sequences", *Cell*, (1993), 72:767–778.

Subramanyama, M., et al. , "Mechanism Of Hiv–1 Tat Induced Inhibition Of Antigen–Specific T Cell Responsiveness", *J Immunol*, (1993), 150(6):2544–2553.

Demuth, H.U., et al., "Design Of (Omega–N–(O–Acyl)Hydroxy Amid) Aminodicarboxylic Acid Pyrrolidides As Potent Inhibitors Of Proline–Specific Peptidases", *FEBS Lett,* (1993), 320:23–27.

Janeway, C., et al., "Immunobiology—The Immune System In Health And Disease", *Current Biology LTD,* (1994), Chapter 12, pp 1–35.

Brady, L., and Doson, G., "Reflections On A Peptide", *Nature,* (1994), 368:692–693.

Nicola, N, et al., "Guidebook To Cytokines And Their Receptors", *Sambrook and Tooze Publication,* (1994), pp. 1–257.

Perstorp Biotec Company, "Molecular Biology Catalog", (1994).

Jameson, B.A., et al., "A Rationally Designed CD4 Analogue Inhibits Experimental Allergic Encephalomyelitis Encephalomyelitis", *Nature,* (1994), 368:744–746.

Mosmann, T.R., "Cytokine Patterns During The Progression To Aids", *Science,* (1994), 265:193–194.

Seed, B., "Making Agonists Of Antagonists", *Chemistry & Biology,* (1994), 1:125–129.

Austin, D.J., et al., "Proximity Versus Allostery: The Role Of Regulated Protein Dimerization In Biology", *Chemistry & Biology,* (1994), 1:131–136.

Sudmeier, J.L., et al., "Solution Structures Of Active An Inactive Forms Of The DP IV (CD26) Inhibitor Pro–Boropro Determined By NMR Spectroscopy", *Biochemistry,* (1994), 33:12427–12438.

Kubota, T., et al., "Dipeptidyl Peptidase Iv (Dp Iv) Activity In Serum And On Lymphocytes Of MRL/ Mp–lpr/lpr Mice Correlates With Disease Onset", *Clin Exp Immunol,* (1994), 96:292–296.

Snow, R.J., et al., "Studies On Proline Boronic Acid Dipeptide Inhibitors Of Dipeptidyl Peptidase Iv: Identification Of A Cyclic Species Containing A B–N Bond", *J. Am. Chem Soc,* (1994), 116:10860–10869.

Günther, U.L., et al., "Solution Structures Of The Dp Iv (Cd26) Inhibitor Val–Boropro Determined By NMR Spectroscopy", *Magnetic Resonance in Chem,* (1995), 33:959–970.

Subramanyam, M., et al., "CD26, At–Cell Accessory Molecule Induction Of Antigen–Specific Immune–Suppression By Inactivation Of CD26: A Clue To The Aids Paradox?", in *Dipeptidyl Peptidase IV(CD26) in Metabolism and Immune Response,* (1995), Ed. B. Fleischer: 155–162.

Schmitz T, et al., "Potentiation Of The Immune Response In Hiv–1+ Individuals", *J Clin Invest,* (1996), 97:1545–1549.

Aguila, H.L., et al., "From Stem Cells To Lymphocytes: Biology And Transplantation", *Immun Rev,* (1997), 157:13–40.

Dupont, B., "Immunology Of Hematopoietic Stem Cell Transplantation: A Brief Review Of Its History", *Immun Rev,* (1997), 157:5–12.

Bodansky, M., "Peptide Chemistry, A Practical Textbook", *Springer–Verlag,* (1988) 1–9.

Boros, L.G., et al., "Fluoroolefin Peptide Isosteres–Tools For Controlling Peptide Conformations", *Tetrahedron Letters,* (1994), 35:6033–6036.

Goodman, M., and Chorev, M., "On The Concept Of Linear Modified Retro–Peptide Structures", *Accounts of Chemical Research,* (1979), 12:1–7.

Guichard, G., et al., Partially Modified Retro–Inverso Pseudopeptides As Non–Natural Ligands For The Human Class I Histocompatibility Molecule HLA–A2, *J Med Chem,* (1996), 39:2030–2039.

Jardetzky, T.S., et al., Three–Dimensional Structure Of A Human Class II Histocompatibility Molecule Complexed With Superantigen, *Nature,* (1994), 368:711–718.

Zimmerman, D.H., et al., "A New Approach To –T–Cell Activation: Natural And Synthetic Conjugates Capable Of Activating T Cells", *Vaccine Res,* (1996), 5:91–102.

Zimmerman, D.H., et al., "Immunization With Peptide Heteroconjugates Primes A T Helper Cell . . . " *Vaccine Res,* (1996), 5:103–118.

Welch, J.T., and Lin J., Fluoroolefin Containing Dipeptide Isoteres As Inhibitors Of Dipeptidyl Peptidas IV (CD26), *Tetrahedron,* (1995), 52:291–304.

Duke–Cohan, J.S., et al., "Targeting Of An Activated T–Cell Subset Using A Bispecific Antibody– Toxin Conjugate Directed Against CD4 and CD26", *Blood,* (1993), 82:2224–2234. Abstract.

Tanaka, et al., "Direct Association of Adenosine Deaminase with a T Cell Activation Antigen, CD26" *Science* 261(5120):466–469 (1993) Abstract.

Hegen, M., et al., "Function of dipeptidyl peptidase IV (Cd26, Tp103) in transfected human T–cells", *Cell Immunol.* 146(2):249–260 (1993) Abstract.

Hegen, M., et al., Enzymatic activity of Cd26 (dipeptidylpeptidase IV) is not required for its signalling function in T cells), *Immunobiology,* 189(5):483–493 (1993) Abstract.

Tanake, T., et al., "The Costmulatory Activity Of The Cd26 Antigen Requires Dipeptidyl Peptidase Iv Iv Enzymatic Activity", *Proc Natl Acad Sci U S A,* (1993), 90:4586–4590. Abstract.

Tanaka, T., et al., "Cloning And Functional Expression Of The T Cell Activation Antigen CD26", *J Immunol,* 149:481–486. (1992) Abstract.

Scharpe, S., et al., "Purified And Cell–Bound Cd26: Enzymatic Inhibition, Antibody Binding Profile, And Expression On T Cells In Relation To Other Surface Markers", *Verh K Acad Geneeskd Belg,* (1994), 56:537–559. Abstract.

Kameoka, J., et al., "Differential Cd26–Mediated Activation Of The Cd3 And Cd2 Pathways After Cd6–Depleted Allogeneic Bone Marrow Transplantation", *Blood,* (1995), 85:1132–1137. Abstract.

Mittrucker, H.W., et al., "The Cytoplasmic Tail Of The T Cell Receptor Zeta Chain Is Required For Signaling Via CD26", *Eur J Immunol,* (1995), 25:295–297. Abstract.

Morimoto, C., et al., 1F7 "A Novel Cell Surface Molecule, Involved In Helper Function Of CD4 cells", *J. Of Immunol.,* 143:34030–3439 (1989) and published erratum appears in *J. Immunology* 144 (5):2027 (Mar. 1990). Abstract.

Barton, R. W.J., et al., "Binding Of The T Cell Activation Monoclonal Antibody Tal To Dipeptidyl Peptidase IV", *J. of Leukocyte Biology* 48:291–296 (1990). Abstract.

Bristol, L.A., et al., "Thymocyte Costimulating Antigen Is CD26 (Dipeptidyl–Peptidase IV), Co–stimulation Of Granulocyte, Macrophage, T Lineage Cell Proliferation Via CD26," *J. Immunol.* 149:367–372 (1992). Abstract.

Bristol, L.A., et al., "Characterization Of A Novel Rat Thymocyte Costimulating Antigen By The Monoclonal Antibody 1.3", *J. Immunol.* 148:332–338 (1992). Abstract.

Fleisher, B., et al., "Triggering Of Cytotoxic T Lymphocytes And NK Cells Via The Tp103 Pathway Is FIFF Dependent On the Expression Of The T Cell Receptor/CD3 Complex", *J. Of Immunol.* 141:1103–1107 Abstract (not dated).

Hegen, M., et al., "The T Cell Triggering Molecule Tp103 . . . " *J. Immunol.* 144:2908–2914 (1990). Abstract.

Darmoul, D., et al., "Dipeptidyl Peptidase IV (CD26) Gene Expression In Enterocyte–like Colon Cancer Cell Lines HT–29 And Caco–2: Cloning Of The Complete Human Coding Sequence And Changes Of Dipeptidyl Peptidase IV mRNA Levels During Cell Differentiation," *J. Of Biological Chemistry* 267:4824–33 (1992). Abstract.

Tanaka, T., "Cloning and Functional Expression of the T cell Activation Antigen CD26" *J. Immunol.* 150(5):2090 Abstract (not dated).

Heins, J., et al., "Mechanism Of Proline–Specific Proteinases: (I) Substrate Specificity of Dipeptidyl Peptidase Peptidase IV From Pig Kidney And Prolin–Specific Endopeptidase From Flavobacterium Meningosepticum", *Biochimica Et Biophysica Acta* 954:161–169 (1988). Abstract.

Schon, E., et al., "The Dipeptidyl Peptidase IV, A Membrane Enzyme Involved In The Proliferation . . . Lymphocytes", *Biomedica Biochimica Acta* 44 (1985). Abstract.

Schon, E., et al., "Dipeptidyl Peptidase IV In Human T Lymphocytes. An Approach To The Role Of A Membrane Peptidase In The Immune System", *Biomedica Biochimica Acta* 45:1523–1528 (1986) Abstract.

Schon, E., et al., "The Role Of Dipeptidyl Peptidase IV In Human T Lymphocyte Activation. Inhibitors And Antibodies Against Dipeptidyl Peptidase IV Suppress Lymphocyte Proliferation And Immunoglobulin Synthesis In Vitro", *Eur. J. Of Immunol.* 17:1821–1826 (1987). Abstract.

Freeman, et al., "*Clinical & Experimental Immunology*" 88 (2): 275–279 (May 1992). Abstract.

Perry, et al., *Eur. J. Of Immunol.* 26 (1): 136–141 (Jan. 1996). Abstract.

Goodstone, et al., *Annals Of The Rheumatic Diseases* 55 (1):40–46 (Jan. 1996). Abstract.

Hall, et al., *Seminars In Dermatology,* 10 (3):240–245 (Sep. 1991). Abstract.

Karges, et al., *Molecular Aspects Of Medicine* 16(2):79–213 (1995). Abstract.

Short, et al., *Nephrology, Dialysis, Transplantation* 7 Supp.1:121 (1992). Abstract.

Kalluri, et al., *J. Of The American Society Of Nephrology* 6 (4):1178–1185 (Oct. 1995). Abstract.

Mullins, et al., *J. Clinical Investigation* 96 (1): S37–40 (Jul. 1996). Abstract.

El Far, et al., *J. Of Neurochemistry,* 64 (4): 1696–1702 (1995). Abstract.

James, et al., *Clinical & Experimental Rheumatology,* 13 (3):299–305 (1995). Abstract.

Van Noort, et al., *Nature* 375 (6534):798–801 (Jun 29, 1995). Abstract.

Protti, et al., *Immunol. Today* 14 (7): 363–368 (Jul. 1993). Abstract.

Linington, et al., *Eur. J. Of Immunol.* 22 (7): 1813–1817 (Jul. 1992) Abstract.

Chan, et al., *Archives Of Ophthalmology* 113 (5): 597–600 (1995). Abstract.

Liu, et al., *J. Of Immunol.* 155 (11): 5449–5454 (1995). Abstract.

Uibo, et al., *J. Autoimmunity* 7 (3): 399–411 (1994). Abstract.

Kokawa, et al., *Eur. J. Of Hematology* 50 (2): 74–80 (1993). Abstract.

Daw, et al., *J. Of Immunol.* 156 (2): 818–825 (1996). Abstract.

Chazenbalk, et al., *J. Clin. Endocrinol. Metab.* 77(6):1715–1718 Abstract (not dated).

Hart, et al., *Pharmaceutical Biotechnology* 6:821–845 (1995). Abstract.

Lopez, et al., *Vaccine* 12 (7):585–591 (1994). Abstract.

Reynolds, et al., *J. Immunol.* 152 (1):193–200 (1994). Abstract.

Nardelli, et al., *J. Immunol.* 148 (3): 914–920 (1992). Abstract.

Darcy, et al., *J. Immunol.* 149 (11):3636–3641 (1992). Abstract.

Ritu, et. al., *Vaccine* 10 (11): 761–765 (1992). Abstract.

Ikagawa, et al., *J. Allergy Clin. Immunol.* 97 (1 Pt 1): 53–64 (Jan. 1996). Abstract.

Brander, et al., *J. Immunol.* 155 (5):2670–2678 (Sep. 1, 1995). Abstract.

O'Brien, et al., *Immunology* 86 (2):176–182 (1995). Abstract.

Zhu, X., et al., *J. Immunol.* 155 (10):5064–5073 (1995). Abstract.

Dudler, et al., *Eur. J. Of Immunol.* 25 (2):538–542 (1995). Abstract.

Bungy, et al., *Eur. J. Immunol.* 24 (9):2098–2103 (1994). Abstract.

Shimojo, et al., *Int'l. Archives Allergy Immunol.* 105 (2):155–161 (1994). Abstract.

Kelly, T.A., et al., "The Efficient Synthesis And Simple Resolution Of A Proline Boronate Ester Suitable For Enzyme Inhibition Studies", *Tetrahedron* 49:1009–1016 (1993). Abstract.

Watson, J.D., "Continuous Proliferation Of Murine Antigen Specific Helper T Lymphocytes In Culture", *J. Exp. Med.* 150(6):1510 (1979). Abstract.

Kuchroo, V.K., et al., "Induction Of Experimental Allergic Encephalomyelitis By Myelin Proteolipid–Protein–Specific T Cell Clones And Synthetic Peptides", *Pathobiology* 59:305–312 (1991). Abstract.

Kuchroo, V.K., et al., "T–cell Receptor Alpha Chain Plays a Critical Role In Antigen–Specific Suppressor Cell Function", *Proc. Natl. Acad. Sci. USA* 88:8700–8704 (1991). Abstract.

Kuchroo, V.K., et al., "Experimental Allergic Encephalomyelitis Medicated By Cloned T Cells Specific For A Synthetic Peptide of Myeline Proteolipid Protein. Fine Specificity And T Cell Receptor V Beta Usage", *J. Immunol.* 148(12):3776–3782 (1992). Abstract.

Kuchroo, V.K., et al., "Cytokines And Adhesion Molecules Contribute To The Ability Of Myelin Proteolipid Protein––Specific T Cell Clones To Mediate Experimental Allergic Encephalomyelitis", *J. Immunol.* 151:4371–4382 (1993). Abstract.

Kuchroo, V.K., et al., "T Cell Receptor (TCR) Usage Determines Disease Susceptibility In Experimental Autoimmune Encephalomyelitis: Studies with TCR V Beta .2 Transgenic Mice", *J. Exp. Med.* 179(5):1659–1664 (1994). Abstract.

Kuchroo, V.K. "A Single TCR Antagonist Peptide Inhibits Experimental Allergic Encephalomyelitis Mediated By A Diverse T Cell Repertoire", *J. Immunol.*. 153(7):3326–3336 (1994). Abstract.

Jorgensen, J.L., et al., "Molecular Components Of T–Cell Recognition," *Annu. Rev. Immunol.* 10:835–873 (1992). Abstract.

Wyse–Coray, T., et al., "Use Of Antibody/Peptides Constructs Of Direct Antigenic Peptides To T Cells: Evidence For T Cells Processing And Presentation", *Cell. Immunol.*, 139 (1):268–73 (1992). Abstract.

Panina–Bordignon, P., et al., "Universally Immunogenic T Cell Epitopes: Promiscuous Binding To Human MHC Class II And Promiscuous Recognition By T Cells", *Eur. J. Immunol.* 19(12):2237–2242 (1989). Abstract.

Ebenbichler, C., et al., "Structure–function Relationships Of The HIV–1 Envelope V3 Loop Tropism Determinant: Evidence For Two Distinct Conformations", *Aids* 7(5):639–46 (1993). Abstract.

Linsley, P.S., et al., "Effects Of Anti–gp120 Monoclonal Antibodies On CD4 Receptor Binding By The Env Protein Of Human Immunodeficiency Virus Type 1", *J. Virol.* 62(10):3695–3702 (1989). Abstract.

Rini, J.M., et al., "Crystal Structure Of A Human Immunodeficiency Virus Type 1 Neutralizing Antibody, 50.1, In Complex With Its V3 Loop Peptide Antigen", *Proc. Natl. Acad. Sci.* USA 90(13):6325–9 (1993).

Dang, N.H., et al., "Cell Surface Modulation Of CD26 By Anti–1F7 Monoclonal Antibody: Analysis Of Surface Expression And Human T Cell Activation", *J. Immunol.* 145(12):3963–3971 (1990). Abstract.

De Caestecker, M.P., et al., "The Detection Of Intercytoplasmic Interleukin 1 (Alpha) Expression In Human Monocytes Using Two Colour Immunofluorescence Flow Cytometry", *J. Immunol. Methods* 154(1):11–20 (1992). Abstract.

Fauci, A.S., "The Human Immunodeficiency Virus: Infectivity And Mechanisms Of Pathogenesis", *Science* 239(4840):617–22 (1988). Abstract.

Kinder, D., et al., "Analogues of Carbamyl Aspartate as Inhibitors . . . " *J. Med. Chem.*, (1990), 33:819–823.

Wijdenes et al., "Monoclonal Antibodies (mAb) against gp130 Imitating Cytokines Which use the gp130 for Signal Transduction", (Jul., 1995), p. 303. Abstract.

Blumenstein et al., Biochem. Biophys. Res. Comm. 163(2):980–987. (not dated).

Luftig et al., "Update on viral Pathogenesis," *ASM News* (1990) 56(7):366–368.

Jiang, J.D. et al., "Inhibition of Human Immunodeficiency Virus Type 1 Infection in a T–Cell Line (CEM) by New Dipeptidyl–Peptidase IV (CD26) Inhibitors," *Res. Virol,* 1997, 148, pp. 255–266.

Coutts, Simon J. et al., "Structure–Activity Relationships of Boronic Acid Inhibitors of Dipeptidyl Peptidase IV. 1. Variation of the $P_2$ Position on Xaa–boroPro Dipeptides," *J. Med. Chem.* (1996) 39:2087–2094.

Ostresh, J.M. et al., "Generation and Use of Nonsupport–Bound Peptide and Peptidomimetric Combinational Libraries," *Methods of Enzymology,* 267(13):220–234 (1996).

Reinhold, et al., "Inhibitors of dipeptidyl peptidase IV (DP IV, CD26) induces secretion of transforming growth factor–β1 (TGF–β1) in stimulated mouse splenocytes and thymocytes" *Immunol. Letters* 58:29–35 (1997).

Ansorge, et al., "CD26/Dipeptidyl Peptidase IV in Lymphocyte Growth Regulation", *Adv Exp Med Biol.* (1997) 421:127–40.

Schon, et al., "Dipeptidyl peptidase IV in human lymphocytes impaired induction of interleukin–2 and gamma interferon due to specific inhibition of dipeptidyl peptidase IV", *Scandinavian J. of Immunol.* 29:127–132 (1989).

Wang, et al., "Epitope specificity of monoclonal anti–beta 2–glycoprotein I antibodies derived from patients with the antiphospholipid syndrome", *J. Immunol.,* 155(3):1629–36 (1995).

Wucherpfenning, et al., "Structural basis for major histocompatibility complex (MHC)–linked susceptibility to autoimmunity: charged residues of a single MHC binding–pocket confer selective presentation of self–peptides in pemphigus vulgaris", *Proc. Natl. Acad. Sci.* USA, 92(25):11935–9, (1995).

Huges, R.A. and Keat, A.C., "Reiter's syndrome and reactive arthritis: a current view", *Semin Arthritis Rheum,* 24(3):190–210 (1994).

Chaenbalk, et al., "Human organ–specific autoimmune disease . Molecular cloning and expression of an autoantibody gene repertoire for a major autoantigen reveals an antigenic immunodominant region and restricted immunolglobulin gene usage in the target organ", *J. Clin. Invest.,* 92(1):62–74 (1993).

Zhu, et al., "T cell epitope mapping of ragweed pollen allergen Ambrosia arteisiifolia (Amb t 5) and the role of free sulfhydryl groups in T cell recognition" *J. Immunol.,* 155(10):5064–73, 1995.

Ogawa, et al., "Alpha–subunit of beta–conglycinin, an allergenic protein recognized by IgE antibodies of soybean–sensitive patients with atopic dermatitis", *Biosci. Biotechnol. Biochem,* 59(5):831–3 (1995).

Okano, et al., "Population analysis of cellular responses to synthetic peptides of Der p II, a major allergen molecule of Dermatophagoides pteronyssinus, in allergic and nonallergic subjects", *Allergy,* 49(6):436–41 (1994).

Mathew, et al., "The gene for fibroblast activation . . . " *Genomics,* 25:335–337 (1995).

Nakamura, et al., "Bronchial Epithelial Cells Regulate Fibroblast Proliferation" *Am. J. Physiol.,* (1995) 269(3 Pt 1):377–87 Abstract.

Chen, W.T., "Proteases Associated With Invadopodia, And Their Role In Degradation Of Extracellular Matrix" *Enzyme Protein,* (1996) 49(1–3):59–71 Abstract.

Niedermeyer, et al., "Mouse Fibroblast Activation Protein: Molecular Cloning, Alternative Splicing And Expression In The Reactive Stroma Of Epithelial Cancers" *Int. J. Cancer,* (1997) 2:71(3):383–9 Abstract.

Welt, et al., "Antibody Targeting In Metastatic Colon Cancer: A Phase I Study Of Monoclonal Antibody F19 Against Cell–Surface Protein Of Reactive Tumor Stromal Fibroblasts" *J. Clin. Oncol.,* (1994) 12(6):1193–203 Abstract.

Ueta, Y. et al., "Lung Fibroblast Growth–Stimulating Activity Of Serine Protein" *Nihon Kyobu Shikkan Gakkai Zasshi* (1993) 31(10):1279–84 Abstract.

Rettig, et al., "Regulation And Heteromeric Structure Of The Fibroblast Activation Protein In Normal And Transformed Cells Of Mesenchymal Neuroectodermal Origin" *Cancer Res.,* (1993) 53:3327–3335.

Rettig, et al., "Fibroblast Activation Protein: Purification, Epitope Mapping And Induction By Growth Factors" *Int. J. Cancer,* (1994) 58:385–392.

Rettig, et al., "Cell–Surface Glycoproteins Of Human Sarcomas: Differential Expression In Normal And Malignant Tissues And Cultured Cells" *Proc. Natl. Acad. Sci.,* USA (1988) 85:3110–3114.

Niedermeyer, et al., "Mouse Fibroblast–Activation Protein: Conserved Fap Gene Organization And Biochemical Function As A Serine Protease" *Eur. J. Biochem.,* (198) 254:650–654.

Blezinger, et al., "Systemic Inhibition Of Tumor Growth And Tumor Metastases By Intramuscular Administration Of The Endostatin Gene" *Nature Biotech.,* (1999) 17:343–348.

Scanlan, et al., "Molecular Cloning Of Fibroblast Activation Protien α, A Member Of The Serine Protease Family Selectively Expressed In Stromal Fibroblasts Of Epithelial Cancers" *Proc. Natl. Acad. Sci.,* USA (1994) 91:5657–5661.

Pineiro–Sanchez, et al., "Identification Of The 170–kDa Melanoma Membrane–Bound Gelatinase (Seprase) As A Serine Integral Membrane Protease" *J. Biol. Chem.,* (1997) 272:12:7595–7601.

Goldstein, et al., "Molecular Cloning Of Seprase: A Serine Integral Membrane Protease From Human Melanoma" *Biochim Biophy Acta,* (1997) 1361:11–19.

Garin–Chesa, P. et al., "Cell Surface Glycoprotein Of Reactive Stromal Fibroblasts As A Proteintial Antibody Target In Human Epithelial Cancers" *Proc. Natl. Acad. Sci.* USA (1990) 87:7235–7239.

Bristol, et al., "Inhibition of CD26 Enzyme Activity with Pro–boropro Stimulates Rat Granulocyte/Macrophage Colony Formation and Thymocyte Proliferation in Vitro" *Blood,* 85(12):3602–3609 (1995).

International Search Report of PCT/US00/14505, mailed Aug. 24, 2000.

Abbott CA, et al., *FEBS Lett.* Sep. 1999 24;458(3):278–84. Abstract Only.

Aytac, U., et al., *Cancer Res.,* 61(19):7204–7210 (2001), Abstract Only.

Bensaadi, N., et al., *Int. J. Pancreatol.,* 4(4):391–406 (1989). Abstract Only.

Buhling, F., et al., *Immunol. Lett.* 45(1–2):47–51 (1995) Abstract Only.

Burchardt, U., et al., *Z. Urol. Nephrol.* 79(10):587–93 (1986). Abstract Only.

Carbone, A., et al., *Hum. Pathol.* 25(12):1360–5 (1994), Abstract Only.

Gallegos ME, et al.,. *Neurochem Res* Dec. 1999;24(12):1557–61. Abstract Only.

Gotze, D., et al., *Folia Haematol. Int. Mag. Klin. Morphol. Blutforsch.* 112(2):233–40 (1985). Abstract Only.

Harland, C., et al., *Clin. Exp. Immunol.* 74(2):201–205 (1988), Abstract Only.

Hass, GM., et al., *Hybridoma,* 20(4):231–6 (2001). Abstract Only.

Hersey, P. *Expert Opin. Investig. Drugs* 11(1):75–85 (2002).

Kanai K, et al., *Acta Pharm Hung.* Nov. 1999;69(5):240–6. Hungarina, English language Abstract Only.

Kinder, DH., et al., *Invasion Metastasis.* 12(506):309–19. (1992). Abstract Only.

Labuda, T., et al., *Int. Immunol.* 7(9):1425–32 (1995). Abstract Only.

Lemez, P., et al., *Haematologia (Budap),* 20(3):165–70, (1987), Abstract Only.

Maes, M., et al., *Neuropsychopharmacology.* 24(2):130–40. (2001). Abstract Only.

Morimoto, C., et al., *J. Immunol.* 143(11):3430–9 (1989), Abstract Only.

Morrison, ME, et al., *J. Exp. Med.* 177(4):1135–43 (1993). Abstract Only.

Novelli, M., et al., *Br. J. Dermatol.* 134(6):1052–6 (1996), Abstract Only.

Pethiyagoda, CL., et al., *Clin. Exp. Metastasis.* 18(5):391–400. (2000). Abstract Only.

Reinhold, D., et al., *Immunobiology.* 192(1–2):121–36 (1994). Abstract Only.

Riemann, D., et al., *Clin. Exp. Immunol.* 100(2):277–83 (1995). Abstract Only.

Ruiz, P., et al., *Cytometry.* 34(1):30–5 (1998) Abstract Only.

Shinoda, M., et al., *Behav. Brain Res.* 99(1):17–25 (1999). Abstract Only.

Stange, T., et al., *Eur. J. Histochem.* 44(2):157–64 (2000). Abstract Only.

Szeltner Z, *Protein Sci.* Feb. 2000;9(2):353–60. Abstract Only.

Van Den Oord, JJ *Br. J. Dermatol.* 138(4):615–21 (1998). Abstract Only.

Verstrovsek, S., et al., *Oncology (Huntingt).* 14(6 Suppl. 2): 17–23 (2000). Abstract Only.

Wesley, U.V., et al., *J. Exp. Med.* 190(3):311–322 (1999).

Williams, RS., et al., *EMBO J.,* 18(10):2734–45 (1999) Abstract Only.

Schon, E, et al., *Acta. Hyistochem. Suppl.,* 33:131–138 (1986) Abstract Only.

Ariga, N. et al., "Stromal expression of fibroblast activation protein/seprase, a cell membrane serine proteinase and gelatinase, is associated with longer survival in patients with invasive ductal carcinoma of breast" *Int. J. Cancer,* Jan. 20, 2001, 95(1):67–72

Goldstein, L.A., et al., "Identification of an Alternatively Spliced Seprase mRNA that Encodes a Novel Intracellular Isoform" *The Journal of Biological Chemistry,* vol. 275, No. 4, Jan., 2000, pp. 2554–2559.

McCaughan, G.W. et al., "Molecular pathogenesis of liver disease: an approach to hepatic inflammation, cirrhosis and liver transplant tolerance" *Immunological Reviews 2000,* vol. 174: 172–191.

Park, J.E., et al., "Fibroblast Activation Protein, a Dual Specificity Serine Protease Expressed in Reactive Human Tumor Stromal Fibroblasts" *The Journal of Biological Chemistry,* vol. 274, No. 51, Dec. 1999, pp. 36505–36512.

Rettig, W.J., et al., "Differential Expression of Cell Surface Antigens and Glial Fibrillary Acidic Protein in Human Astrocytoma Subsets" *Cancer Research* 46:6406–6412, Dec. 1986.

Sun, S. et al., "Expression purification, and kinetic characterization of full–length human fibroblast activation protein" *Protein Expr. Purif.* Mar. 2002, 24(2):274–281 (Abstract Only).

\* cited by examiner

ANTI-TUMOR AGENTS

RELATED APPLICATIONS

This application claims priority under 35 U.S.C. § 119(e) to the provisional patent application entitled "Anti-Tumor Agents" filed May 25, 1999, and assigned Ser. No. 60/135,861, the entire contents of which are incorporated herein by reference.

FIELD OF THE INVENTION

This invention relates to methods for the treatment of abnormal proliferative disorders. The methods involve administering certain compounds to inhibit proliferation and angiogenesis in an abnormal proliferative cell mass.

BACKGROUND OF THE INVENTION

Abnormal cell proliferation is usually characterized by an increased rate of division and in some cases uncontrolled growth. One example of a proliferative cell disorder is a tumor. In addition to posing a serious health risk in and of themselves, primary malignant tumors are particularly problematic given their tendency to invade surrounding tissues and metastasize to distant organs in the body. To date, the most frequently used methods for treating neoplasia, especially solid tumor forms of neoplasia, include surgical procedures, radiation therapy, drug therapies, and combinations of the foregoing. These methods involve significant risk (e.g., of infection, death) to the patient. More importantly, the probability of eliminating all malignant cells is small particularly if the zone of malignant growth is not well defined or if the primary tumor has metastasized by the time of surgery. Achieving therapeutic doses effective for treating the cancer is often limited by the toxic side effects of the anti-cancer agent on normal, healthy tissue. An ideal anti-cancer agent has tissue specificity, thereby reducing side-effects on normal (dividing) cells.

Recently, a model of anticancer therapy has been proposed and validated that targets the vasculature of solid tumors rather than the malignant cells themselves. Most, if not all, solid tumors require a blood supply system for oxygenation, nutrient delivery and waste product removal. The need for neovascularization is particularly acute if the tumor is to grow beyond the confines of the normal blood supply system. As a result, tumors which do attain a certain size are able to elicit the growth of new blood vessels from the surrounding endothelial cells, through a process called angiogenesis, through the release of angiogenic factors.

In view of the foregoing, a need exists to identify agents for treating cancer and metastasis.

SUMMARY OF THE INVENTION

The invention solves these and other problems by providing methods and related compositions for treating conditions characterized by abnormal cell proliferation, including, but not limited to, cancer and metastasis. The invention is based, in part, on the observation that compounds of Formula I are able to inhibit the enzymatic activity of fibroblast activation protein-alpha (FAP-α).

In one aspect, the invention provides a method for treating a subject having a condition characterized by abnormal mammalian cell proliferation. The method comprises administering to a subject in need of such treatment, an agent in an amount effective to inhibit the proliferation, wherein the agent is a compound of Formula I:

PR            Formula I wherein P is a targeting group which binds to the reactive site of FAP-α or other post proline-cleaving enzyme and can be a peptide or a peptidomimetic, and wherein R is a reactive group capable of reacting with a functional group in FAP-α or other post proline cleaving enzyme, preferably in the reactive site of FAP-α or other post proline cleaving enzyme. The reactive compound may be selected from the group consisting of organo boronates, organo phosphonates, fluoroalkylketones, alphaketos, N-peptiolyl-O-(acylhydroxylamines), azapeptides, azetidines, fluoroolefins dipeptide isoesteres, peptidyl (alpha-aminoalkyl) phosphonate esters, aminoacyl pyrrolidine-2-nitriles and 4-cyanothiazolidides.

One group of Formula I compounds useful in the invention can be further defined by Formula II

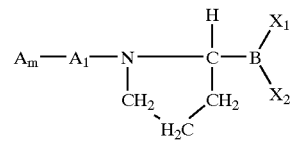

Formula II wherein m is an integer between 0 and 10, inclusive; A and Al may be L- or D-amino acid residues such that each A in $A_m$ (i.e., where m>1) may be a different amino acid residue from every other A in $A_m$; the C bonded to B is in the L-configuration; the bond between $A_1$ and N and, in some embodiments, between $A_1$ and $A_m$, are peptide bonds; and each $X_1$ and $X_2$ is, independently, a hydroxyl group or a group capable of being hydrolyzed to a hydroxyl group in aqueous solution at physiological pH. By "the C bonded to B is in the L-configuration" is meant that the absolute configuration of the C is like that of an L-amino acid. Thus, the

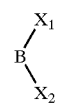

group has the same relationship to the C as the —COOH group of an L-amino acid has to its α carbon. In some embodiments, A and Al are independently proline or alanine residues. In some embodiments, m is 0. In some embodiments, $X_1$ and $X_2$ are hydroxyl groups. In some embodiments, the inhibitor is L-Ala-L-boroPro. In still other embodiments, inhibitor is L-Pro-L-boroPro.

In addition to agents of Formula II, other agents useful in the invention include those in which the proline residue in Formula II is replaced with another amino acid residue such as, for example, lysine, alanine or glycine. As well, derivatives of Formula II in which the boronate group is replaced with a reactive group as described above are also useful in the invention. In preferred embodiments, the agent is Val-boro-Pro.

Some representative agents of Formula I can be further defined by Formula III as follows:

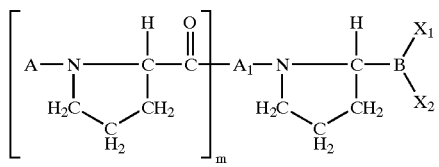

Formula III wherein m is an integer between 0 and 10, inclusive; A and $A_1$ are L-amino acid residues (for glycine there is no such distinction) such that the A in each repeating bracketed unit can be a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH. By "the C bonded to B is in the L-configuration" is meant that the absolute configuration of the C is like that of an L-amino acid.

In general, naturally occurring compounds which contain a chiral center are only in one stereo isomeric form, either D or L. The naturally occurring amino acids are the L stereo isomers; however, the invention embraces amino acids which can be in the D stereo isomer configuration.

In one aspect, the agent of Formula I is administered to a subject in need thereof in an amount effective to inhibit abnormal mammalian cell proliferation. The subjects to be treated are subjects having a condition characterized by abnormal mammalian cell proliferation. In certain embodiments, the subjects preferably are otherwise free of symptoms calling for hemopoietic stimulation and, in particular, are free of symptoms calling for treatment with a compound for stimulating an immune response. In some embodiments, the subjects to be treated do not exhibit symptoms requiring hemopoietic stimulation and have normal or protective levels of hemopoietic cells. The subject to be treated may have normal hemopoietic activity. Included are subjects who are HIV positive but who have normal hemopoietic activity. In another embodiment, the subject is HIV negative. In certain embodiments, the subject are not myeloid or lympfoid suppressed or are not candidates for treatment with an agent which causes such suppression at the time of treatment with the methods of the invention.

The invention is further premised, in part, on the discovery that compounds of Formula I (e.g., Val-boro-Pro) have anti-tumor activity in melanoma and fibrosarcoma.

Thus, in another aspect, the subjects are treated with the agent of Formula I in a manner and in an amount so as to inhibit proliferation of a primary tumor, or to inhibit metastatic spread or growth while minimizing the potential for systemic toxicity. In certain embodiments, the abnormal mammalian cell proliferation is manifested as a tumor. Some conditions intended to be treated by the method of the invention include benign (i.e., non-cancerous), premalignant and malignant (i.e., cancerous) tumors. In some embodiments, the condition characterized by abnormal mammalian cell proliferation is further characterized by the presence of reactive stromal fibroblasts.

In other embodiments, the abnormal mammalian cell proliferation is selected from the group consisting of a carcinoma, a sarcoma, and a melanoma In yet other embodiments, the condition is selected from the group consisting of breast cancer, colorectal cancer, ovarian cancer, prostate cancer, pancreatic cancer, kidney cancer, lung cancer, melanoma and fibrosarcoma. In still other embodiments, the condition is selected from the group consisting of bone and connective tissue sarcomas, examples of which include, but are not limited to, osteosarcoma and fibrosarcoma.

In still other embodiments, the abnormal mammalian cell proliferation is in epithelial cells, meaning that it is epithelial cells which are abnormally proliferating. Some conditions characterized by abnormal mammalian epithelial cell proliferation include adenomas of epithelial tissues such as the breast, colon and prostate, as well as malignant tumors. According to other embodiments of the invention, a method is provided for treating a subject having a metastasis of epithelial origin.

According to some embodiments of the invention, the agent is administered locally. In some embodiments, the agent is targeted to a tumor. This can be achieved by the particular mode of administration. For example, easily accessible tumors such as breast or prostate tumors may be targeted by direct needle injection to the site of the lesion. Lung tumors may be targeted by the use of inhalation as a route of administration.

In some embodiments, the agents may be administered in a systemic manner, via administration routes such as, but not limited to, oral, intravenous, intramuscular and intraperitoneal administration. Systemic administration routes may be preferred, for example, if the subject has metastatic lesions. In other embodiments, the agent is administered in a sustained release formulation.

In administering the compounds of the invention to subjects, dosing amounts, dosing schedules, routes of administration and the like may be selected so as to affect the other known activities of these compounds. For example, amounts, dosing schedules and routes of administration can be selected as described herein, whereby therapeutically effective levels for inhibiting proliferation are provided, yet therapeutically effective levels for restoring hemopoietic deficiency are not provided.

In addition, agents can be selected that are effective as anti-proliferative agents or as anti-angiogenic agents but are relatively ineffective as hemopoietic cell stimulatory or activating agents. Thus, certain subjects who require both hemopoietic stimulation and/or activation and proliferation and/or angiogenic inhibition may be treated with different agents of the invention simultaneously, one each for the desired therapeutic effect, or with a single compound but in different dosages, schedules, and/or route to achieve both hemopoietic stimulation and proliferation inhibition at therapeutic levels.

In some embodiments of the invention, a method is provided in which the agent is administered in combination with an anti-proliferative compound, such as an anti-cancer compound. In another embodiment, the agent is administered in combination with surgery to remove an abnormal proliferative cell mass. In a related embodiment, the agent is administered to a patient who has had surgery to remove an abnormal proliferative cell mass.

In another aspect, the invention provides a method for inhibiting angiogenesis in a subject having a condition characterized by abnormal mammalian cell proliferation comprising administering to a subject in need of such treatment, an agent in an amount effective to inhibit angiogenesis in an abnormal proliferative cell mass, wherein the agent is a compound of Formula I.

In some embodiments, the abnormal mammalian cell proliferation is manifested as a tumor. In another embodiment, the abnormal mammalian cell proliferation is selected from the group consisting of a carcinoma, a sarcoma, and a melanoma. In still another embodiment, the condition characterized by abnormal mammalian cell proliferation is a metastasis. In other embodiments, the condition is selected from the group consisting of breast cancer, colorectal cancer, ovarian cancer, prostate cancer, pancreatic cancer, kidney cancer, lung cancer, melanoma and fibrosarcoma. In another embodiment, the abnormal mammalian cell proliferation is in epithelial cells, meaning that epithelial cells are abnormally proliferating.

In one embodiment, the agent is administered locally. In another embodiment, the agent is targeted to a tumor. In another embodiment, the agent is administered in a sustained release formulation. In yet another embodiment, the agent is administered systemically.

In some embodiments, the agent is administered in combination with surgery to remove an abnormal proliferative cell mass. In other embodiments, the agent is administered to a patient who has had surgery to remove an abnormal proliferative cell mass.

In one embodiment, the agent is administered in combination with an anti-proliferative compound such as an anti-cancer compound. In other embodiments, the agent is administered in combination with an anti-angiogenic compound. In yet other embodiments, the agent is administered with an anti-cancer compound and an anti-angiogenic compound.

In one embodiment, the subject has normal hemopoietic activity. In another embodiment, the subject is HIV negative.

According to still another aspect of the invention, pharmaceutical preparations are provided that comprise an agent of Formula I, as described above, and a pharmaceutically-acceptable carrier. Formula I agents are present in the pharmaceutical preparations in an amount effective for inhibiting proliferation in primary or secondary (e.g., metastatic) malignant lesions. These pharmaceutical preparations may contain the agent of Formula I alone or in combination with other compounds (e.g., anti-cancer compounds and/or anti-angiogenic compounds).

In one aspect, a pharmaceutical preparation is provided comprising an agent of Formula I, at least one other anti-cancer compound (i.e., an anti-cancer compound other than an agent of Formula I), and a pharmaceutically acceptable carrier. In another aspect, a pharmaceutical preparation is provided which comprises an agent of Formula I, at least one other anti-angiogenic compound (i.e., an anti-angiogenic compound other than an agent of Formula I), and a pharmaceutically acceptable carrier.

In other embodiments, anti-cancer cocktails containing the agent of the invention and other anti-proliferative compounds and/or other anti-angiogenic compounds as described herein are also provided. In still other embodiments, the agents of Formula I are used in the preparation of a medicament for treating subjects having conditions characterized by abnormal mammalian cell proliferation.

In still other embodiments, the agent may be targeted to a cell mass (e.g., a tumor) through the use of a targeting compound specific for a particular tissue or tumor type. In some embodiments, the agents of the invention may be targeted to primary or in some instances, secondary (i.e., metastatic) lesions through the use of targeting compounds which preferentially recognize a cell surface marker.

These and other aspects of the invention will be described in greater detail below. Throughout this disclosure, all technical and scientific terms have the same meaning as commonly understood by one of ordinary skill in the art to which this invention pertains unless defined otherwise.

DETAILED DESCRIPTION OF THE INVENTION

Figure 1A:
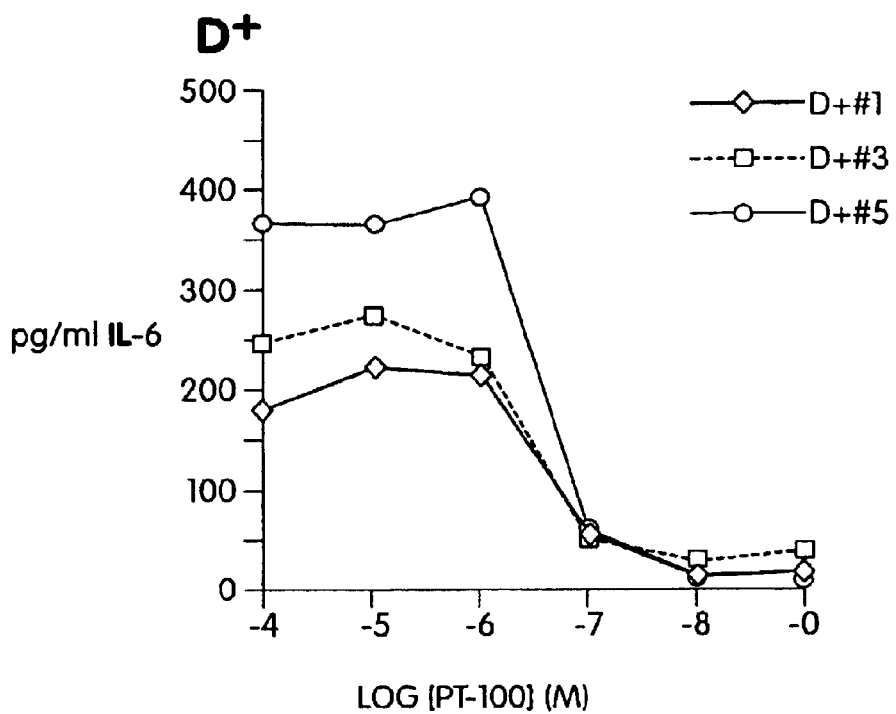
FIG. 1a is a comparison of response of Fischer $D_+$ rat and BM stromal cells to PT-100 in vitro by measurement of interleukin-6 (IL-6) release.

The invention is directed to the inhibition of cellular proliferation and angiogenesis in conditions characterized by abnormal, unwanted mammalian cell proliferation. The invention is useful, inter alia, in the treatment of proliferative disorders including benign, pre-malignant and malignant tumors. In certain embodiments, the methods are directed towards the treatment of subjects with carcinoma or metastatic lesions of epithelial origin. The invention is based, in part, on the finding that PT-100, the dipeptide valine-proline-boronic acid, i.e., (ValboroPro), is able to inhibit fibroblast activation protein (FAP-α), and also exhibits anti-tumor activity against cancers such as, for example, melanoma and fibrosarcoma According to one aspect of the invention, a method is provided for treating a subject having a condition characterized by an abnormal mammalian cell proliferation, using compounds of Formula I:

PR      Formula I wherein P is a targeting group which binds to the reactive site of FAP-α or other post proline-cleaving enzyme, and R is a reactive group capable of reacting with a functional group in the reactive site of FAP-α or other post proline-cleaving enzyme. Post proline-cleaving enzymes are enzymes which have a specificity for removing Xaa-Pro (where Xaa represents any amino acid) dipeptides from the amino terminus of polypeptides. Examples of post-proline cleaving enzymes include, but are not limited to, CD26, dipeptidyl peptidase IV (DP IV) and dipeptidyl aminopeptidase IV.

The P targeting group can be composed of single or multiple residues of peptide or peptidomimetic nature, provided that such residues do not interfere significantly, and most preferably improve the site-specific recognition of FAP-α or other post proline-cleaving enzyme by the agent of Formula I. In certain embodiments, the portion of the P targeting group that is involved in binding to the reactive site of FAP or other post proline-cleaving enzyme is formed of amino acids and the remaining portion of P is formed of non-amino acid components. According to the particular embodiment, P can be composed wholly of amino acid residues, wholly of non-amino acid substituents, or a combination of both.

In general, the targeting group (i.e., P) is covalently coupled to the reactive group. In some embodiments, the covalent coupling occurs via a carboxyl group at the carboxyl terminal amino acid in the P group. In certain embodiments, P may be 30, 20, 10 or less than 10 residues in length.

The development of phage display libraries and chemical combinatorial libraries from which synthetic compounds can be selected which mimic the substrate of a protease permits the identification of further targeting groups to which an R group can be covalently attached to form a binding moiety which binds or associates with the reactive site of the protease and which forms a complex with a functional group in the protease reactive site. Such libraries can be screened to identify non-naturally occurring putative targeting groups by assaying protease cleavage activity in the presence and absence of the putative phage display library molecule or combinatorial library molecule and determining whether the molecule inhibits cleavage by the protease of a known substrate or of a substrate analog (e.g., a chromophoric substrate analog which is easily detectable in a spectrophotometric assay). Those phage library and/or combinatorial library molecules which exhibit inhibition of, for example, FAP-α, then can be covalently coupled to the reactive groups disclosed herein and again tested to determine whether these novel molecules selectively bind to, for example, FAP-α (e.g., by repeating the above-noted screening assay). In this manner, a simple, high-through-put screening assay is provided for identifying non-naturally occurring targeting groups of the invention.

P targeting groups can be synthesized from peptides or other biomolecules including but not limited to saccharides, fatty acids, sterols, isoprenoids, purines, pyrimidines, derivatives or structural analogs of the above, or combinations thereof and the like. Also envisioned in the invention is the use of targeting groups made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates. Many, if not all, of these compounds can be synthesized using recombinant or chemical library approaches. A vast array of candidate targeting groups can be generated from libraries of synthetic or natural compounds. The methods of the invention utilize this library technology to identify small peptides which bind to protease reactive sites. One advantage of using libraries for inhibitor identification is the facile manipulation of millions of different putative candidates of small size in small reaction volumes (i.e., in synthesis and screening reactions). Another advantage of libraries is the ability to synthesize targeting groups which might not otherwise be attainable using naturally occurring sources, particularly in the case of non-peptide moieties.

Examples of reactive groups useful in the invention include organo boronates, organo phosphonates, fluoroalkylketones, alphaketos, N-peptioyl-O-(acylhydroxylamines), azapeptides, azetidines, fluoroolefins dipeptide isosteres, peptidyl (alpha-aminoalkyl) phosphonate esters, aminoacyl pyrrolidine-2-nitriles and 4-cyanothiazolidides.

It is to be understood that the terms 'agent' or 'agent of the invention' or 'agent of Formula I' are used interchangeably to mean all of the derivatives of Formula I described herein.

Some representative agents of Formula I can be further defined by Formula II as follows:

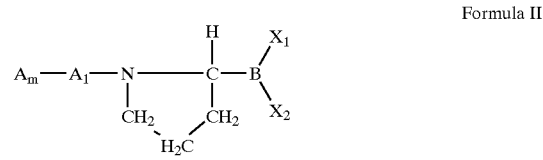

Formula II wherein m is an integer between 0 and 10, inclusive; A and Al may be L- or D-amino acid residues (for glycine there is no such distinction) such that each A in $A_m$ may be an amino acid residue different from another or all other A in $A_m$; the C bonded to B is in the L-configuration; the bond between $A_1$ and N and, in some embodiments, the bond between A and $A_1$ are peptide bonds; and each $X_1$ and $X_2$ is, independently, a hydroxyl group or a group capable of being hydrolyzed to a hydroxyl group in aqueous solution at physiological pH. By "the C bonded to B is in the L-configuration" is meant that the absolute configuration of the C is like that of an L-amino acid. Thus, the

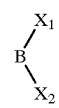

group has the same relationship to the C as the —COOH group of an L-amino acid has to its a carbon. In various embodiments, A and $A_1$ are independently proline or alanine residues; m is 0; $X_1$ and $X_2$ are hydroxyl groups; the inhibitor is L-Ala-L-boroPro; and the inhibitor is L-Pro-L-boroPro.

Other agents useful in the methods and compositions of the invention are derivatives of Formula II in which each and every A in $A_m$ may independently be a non-amino acid residue. Thus, the plurality of A (i.e., $A_m$, wherein m>1) may be a peptide or a peptidomimetic which may include, in whole or in part, non-amino acid residues such as saccharides, fatty acids, sterols, isoprenoids, purines, pyrimidines, derivatives or structural analogs of the above, or combinations thereof and the like. The plurality of A in $A_m$ may also be comprised of a combination of amino acid and non-amino acid residues. It also is possible to substitute non-naturally occurring amino acids, such as 2-azetidinecarboxylic acid or pipecolic acid (which have 6-membered, and 4-membered ring structures respectively) for the proline residue. Representative structures of transition-state analog-based inhibitors Xaa-boroPro of Formula II, include Lys-BoroPro, Pro-BoroPro and Ala-BoroPro in which "boroPro" refers to the analog of proline in which the carboxylate group (COOH) is replaced with a boronyl group [B(OH)$_2$]. Alternative compounds of the invention have an analogous structure in which the boronyl group is replaced by, for example, a phosphonate or a fluoroalkylketone, alphaketos, N-peptioyl-O-(acyihydroxylamines), azapeptides, azetidines, fluoroolefins dipeptide isosteres, peptidyl (alpha-aminoalkyl) phosphonate esters, aminoacyl pyrrolidine-2-nitriles and 4-cyanothiazolidides. It is to be understood that each and every reactive group described herein can be substituted for the reactive group of Formula II (i.e., boronyl group).

All amino acids, with the exception of glycine, contain an asymmetric or chiral carbon and may contain more than one chiral carbon atom. The asymmetric α carbon atom of the amino acid is referred to as a chiral center and can occur in two different isomeric forms. These forms are identical in all chemical and physical properties with one exception, the direction in which they can cause the rotation of plane-polarized light. These amino acids are referred to as being "optically active," i.e., the amino acids can rotate the plane-polarized light in one direction or the other.

The four different substituent groups attached to the Cα carbon can occupy two different arrangements in space. These arrangements are not superimposable mirror images of each other and are referred to as optical isomers, enantiomers, or stereo isomers. A solution of one stereo isomer of a given amino acid will rotate plane polarized light to the left and is called the levorotatory isomer [designated (−)]; the other stereo isomer for the amino acid will rotate plane polarized light to the same extent but to the right and is called dextrorotatory isomer [designated (+)].

A more systematic method for classifying and naming stereo isomers is the absolute configuration of the four different substituents in the tetrahedron around the asymmetric carbon atom (e.g., the α carbon atom). To establish this system, a reference compound was selected (glyceraldehyde), which is the smallest sugar to have an asymmetric carbon atom. By convention in the art, the two stereo isomers of glyceraldehyde are designated L and D. Their absolute configurations have been established by x-ray analysis. The designations, L and D, also have been assigned to the amino acids by reference to the absolute configuration of glyceraldehyde. Thus, the stereo isomers of chiral compounds having a configuration related to that of L-glyceraldehyde are designed L, and the stereo isomers having a configuration related to D-glyceraldehyde are designated D, regardless of the direction in which they rotate the plane-polarized light. Thus, the symbols, L and D, refer to the absolute configuration of the four substituents around the chiral carbon.

In general, naturally occurring compounds which contain a chiral center are only in one stereo isomeric form, either D or L. The naturally occurring amino acids are the L stereo isomers; however, the invention embraces amino acids which can be in the D stereo isomer configuration.

Most amino acids that are found in proteins can be unambiguously named using the D L system. However, compounds which have two or more chiral centers may be in $2^n$ possible stereo isomer configurations, where n is the number of chiral centers. These stereo isomers sometimes are designated using the RS system to more clearly specify the configurations of amino acids that contain two or more chiral centers. For example, compounds such as threonine isoleucine contain two asymmetric carbon atoms and therefore have four stereo isomer configurations. The isomers of compounds having two chiral centers are known as diastereomers. A complete discussion of the RS system of designating optical isomers for amino acids is provided in Principles in Biochemistry, editor A. L. Lehninger, page 99–100, supra. A brief summary of this system follows.

The RS system was invented to avoid ambiguities when a compound contains two or more chiral centers. In general, the system is designed to rank the four different substituent atoms around an asymmetric carbon atom in order of decreasing atomic number or in order of decreasing valance density when the smallest or lowest-rank group is pointing directly away from the viewer. The different rankings are well known in the art and are described on page 99 of Lehninger (supra). If the decreasing rank order is seen to be clock-wise, the configuration around the chiral center is referred to as R; if the decreasing rank order is counter-clockwise, the configuration is referred to as S. Each chiral center is named accordingly using this system. Applying this system to threonine, one skilled in the art would determine that the designation, L-threonine, refers to (2S, 3R)-threonine in the RS system. The more traditional designations of L-, D-, L-allo, and D-allo, for threonine have been in common use for some time and continue to be used by those of skill in this art. However, the R S system increasingly is used to designate the amino acids, particularly those which contain more than one chiral center.

Many of the agents of the invention and methods for their manufacture have been previously disclosed in U.S. Pat. No. 4,935,493, the contents of which are incorporated by reference herein.

As mentioned earlier, the agents, including their individual targeting and reactive groups, may be synthesized using recombinant or chemical library synthesis approaches. Libraries of interest in the invention include peptide libraries, synthetic organic combinatorial libraries, and the like. The artisan or ordinary skill is familiar with the methodology for library and combinatorial chemistry synthesis as well as the screening of such compounds for agents which are useful in the methods of the invention. The use of library technology, such as phage display, and combinatorial chemistry, such as compound array methods, in the synthesis and screening of protease inhibitors has been previously described in U.S. Patent Application entitled "Multivalent Compounds for Crosslinking Receptors and Uses Thereof" filed on Apr. 12, 1999 and assigned U.S. Ser. No. 091290, 376 (pending), the contents of which are incorporated in their entirety by reference. Examples of parallel synthesis mixtures and parallel synthesis methods are provided in U.S. Ser. No. 08/177,497, filed Jan. 5, 1994 and its corresponding PCT published patent application W095/18972, published Jul. 13, 1995 and U.S. Pat. No. 5,712,171 granted Jan. 27, 1998 and its corresponding PCT published patent application W096/22529, which are hereby incorporated by reference.

According to one aspect of the invention, a method for treating a subject having a condition characterized by an abnormal mammalian cell proliferation is provided. As used herein, subject means a mammal including humans, nonhuman primates, dogs, cats, sheep, goats, horses, cows, pigs and rodents. An abnormal mammalian cell proliferation disorder or condition, as used herein, refers to a localized region of cells (e.g., a tumor) which exhibit an abnormal (e.g., increased) rate of division as compared to their normal tissue counterparts.

Conditions characterized by an abnormal mammalian cell proliferation, as used herein, include but are not limited to conditions involving solid tumor masses of benign, pre-malignant or malignant character. Although not wishing to be bound by a particular theory or mechanism, some of these solid tumor masses arise from at least one genetic mutation, some may display an increased rate of cellular proliferation as compared to the normal tissue counterpart, and still others may display factor independent cellular proliferation. Factor independent cellular proliferation is an example of a manifestation of loss of growth control signals which some, if not all, tumors or cancers undergo.

Since the invention is premised, in part, on the finding that agents of Formula I are able to inhibit FAP-α, a cell surface marker of reactive stromal fibroblasts, in one aspect, the invention involves treating conditions involving a tumor mass which contains or is dependent upon the presence of reactive stromal fibroblasts at some point during its development. As used herein, reactive fibroblasts are fibroblasts which have been activated to express proteins such as receptors and growth factors which, in some instances, have a positive effect and, in other instances, have a negative effect on cellular proliferation and growth of the fibroblasts themselves, and other cell types such as malignant cells of a carcinoma or epithelial metastasis.

In one aspect, the invention provides a method for treating subjects having a condition characterized by an abnormal epithelial cell proliferation. Epithelial cells are cells occurring in one or more layers which cover the entire surface of the body and which line most of the hollow structures of the body, excluding the blood vessels, lymph vessels, and the heart interior which are lined with endothelium, and the chest and abdominal cavities which are lined with mesothelium. Examples of epithelium include anterius corneae, anterior epitbelium of cornea, Barrett's epithelium, capsular epithelium, ciliated epithelium, columnar epithelium, epithelium corneae, corneal epithelium, cubical epithelium, cubical epithelium, cuboidal epithelium, epithelium eductus semicircularis, enamel epithelium, false epithelium, germinal epithelium, gingival epithelium, glandular epithelium, glomerular epithelium, laminated epithelium, epithelium of lens, epithelium lentis, mesenchymal epithelium, olfactory epithelium, pavement epithelium, pigmentary epithelium, pigmented epithelium, protective epithelium, pseudostratified epithelium, pyramidal epithelium, respiratory epithelium, rod epithelium, seminiferous epithelium, sense epitheliurn, sensory epithelium, simple epithelium, squamous epithelium, stratified epithelium, subcapsular epithelium, sulcular epitheliurn, tessellated epithelium, transitional epithelium.

One category of conditions characterized by abnormal epithelial cell proliferation is proliferative dermatologie disorders. These include conditions such as keloids, seborrheic keratosis, papilloma virus infection (e.g. producing verruca vulbaris, verruca plantaris, verruca plana, condylomata, etc.) and eczema.

An epithelial precancerous lesion is a skin lesion which has a propensity to develop into a cancerous condition. Epithelial precancerous skin lesions also arise from other proliferative skin disorders such as hemangiomas, keloids, eczema and papilloma virus infections producing verruca vulbaris, verruca plantaris and verruca planar. The symptoms of the epithelial precancerous lesions include skin-colored or red-brown macule or papule with dry adherent scales. Actinic keratosis is the most common epithelial precancerous lesion among fair skinned individuals. It is usually present as lesions on the skin which may or may not be visually detectable. The size and shape of the lesions varies. It is a photosensitive disorder and may be aggravated by exposure to sunlight. Bowenoid actinic keratosis is another form of an epithelial precancerous lesion. In some cases, the lesions may develop into an invasive form of squamous cell carcinoma and may pose a significant threat of metastasis. Other types of epithelial precancerous lesions include hypertrophic actinic keratosis, arsenical keratosis, hydrocarbon keratosis, thermal keratosis, radiation keratosis, viral keratosis, Bowen's disease, erythroplaquia of queyrat, oral erythroplaquia, leukoplakia, and intraepidermal epithelialoma.

Another category of conditions characterized by abnormal epithelial cell proliferation is tumors of epithelial origin.

FAP-α has been observed in tumors of epithelial origin Thus, in one aspect, the invention provides a method for treating subjects having epithelial tumors. Epithelial tumors are known to those of ordinary skill in the art and include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas intended for treatment with the methods of the invention include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidertnoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hürthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the invention are used to treat subjects having cancer of the breast, cervix, ovary, prostate, lung, colon and rectum, pancreas, stomach or kidney.

Other conditions characterized by an abnormal mammalian cell proliferation to be treated by the methods of the invention include sarcomas. Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal [not bone] Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

The methods of the invention are also directed towards the treatment of subjects with melanoma. Melanomas are tumors arising from the melanocytic system of the skin and other organs. Examples of melanoma include lentigo maligna melanoma, superficial spreading melanoma, nodular melanoma, and acral lentiginous melanoma.

Other conditions characterized by an abnormal mammalian cell proliferation are cancers including, but not limited to, biliary tract cancer, endometrial cancer, esophageal cancer, gastric cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

According to other aspects of the invention, a method is provided for treating a subject having an abnormal proliferation originating in bone, muscle orconnective tissue. Exemplary conditions intended for treatment by the method of the invention include primary tumors (i.e., sarcomas) of bone and connective tissue.

The methods of the invention are also directed towards the treatment of subjects with metastatic tumors. In some embodiments, the metastatic tumors are of epithelial origin. Carcinomas may metastasize to bone, as has been observed with breast cancer, and liver, as is sometimes the case with colon cancer. The methods of the invention are intended to treat metastatic tumors regardless of the site of the metastasis and/or the site of the primary tumor. In preferred embodiments, the metastases are of epithelial origin.

The method, in one embodiment, intends to treat subjects free of symptoms calling for hemopoietic stimulation, by administering compounds of Formula I in an amount effective to inhibit proliferation. The ability to treat subjects having symptoms calling for hemopoietic stimulation with the some of compounds (e.g., ValboroPro) described herein has been previously disclosed in U.S. Patent Application entitled "Hematopoietic Stimulation", Ser. No. 09/304,199, filed May 3, 1999, now issued as U.S. Pat. No. 6,300,314, issued Oct. 9, 2001, the contents of which are incorporated herein in their entirety by reference. Thus, the instant invention intends, in certain embodiments, to treat subjects at a time when they are free of symptoms requiring hemopoietic stimulating treatment or to treat subjects who have such symptoms with amounts or dosages or administration schedules that differ from those used to protect or restore normal or protective levels of hemopoietic cells. A subject who has previously experienced a need for hemopoietic stimulation but has since recovered its hemopoietic cells to normal or at least protective levels may still be treated by the methods described herein.

As used herein, the terms hemopoietic and hematopoietic are used interchangeably to mean all blood cells including myeloid and lymphoid cells. Myeloid cells include erythrocytes (i.e., red blood cells), macrophages, monocytes, granulocytes including neutrophils, eosinophils and basophils, mast cells, megakaryoctyes, platelets and dendritic cells, and lymphoid cells include T and B lymphocytes, thymic dendritic cells and natural killer (NK) cells. Hemopoietic stimulation, as used herein, refers to the increase in hemopoietic cell numbers or activity to normal or protective levels.

An example of a symptom calling for hemopoietic stimulation is hemopoietic cell numbers below normal or protective levels. A "normal" level as used herein may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of hematopoietic cell disorders. Such "normal" levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value.

In general, the normal range for neutrophils is about 1800–7250 per $\mu$l (mean –3650); for basophils 0–150 per $\mu$l (mean –30); for eosinophils 0–700 per $\mu$l (mean –150); for macrophages and monocytes 200–950 per $\mu$l (mean –430); for lymphocytes 1500–4000 per $\mu$l (mean –2500); for erythrocytes $4.2 \times 10^6$–$6.1 \times 10^6$ per $\mu$l; and for platelets $133 \times 10^3$–$333 \times 10^3$ per $\mu$l. The foregoing ranges are at the 95% confidence level.

In connection with certain conditions, the medical conmuunity has established certain preselected values. For example, mild neutropenia is characterized as having a count of between 1000 and 2000 per $\mu$l, moderate neutropenia at between 500 and 1000 per $\mu$l and severe neutropenia at below 500 per $\mu$l. Likewise, in adults, a lymphocyte count at less than 1500 is considered a medically undesirable condition. In children, the value is less than 3000. Other preselected values will be readily known to those of ordinary skill in the art.

A protective level of hematopoietic cells is the number of cells required to confer clinical benefit to the patient. The required level can be equal to or less than the "normal level". Such levels are well known to those of ordinary skill in the art. For example, a protective level of neutrophils is above 1000, preferably, at least 1500.

Thus the methods of the invention, according to some embodiments, are directed towards subjects who possess normal or protective levels of hemopoietic cells, as described herein. Subjects with normal or protective levels of hemopoietic cells are considered to have normal hemopoietic activity. Likewise, in some embodiments, the invention is directed for use in subjects who are not immunocompromised. As used herein, the terms irnuunocompromised and immunosuppressed are used interchangeably. An example of an imrnmunocompromised subject is one infected with HIV and experiencing AIDS-related symptoms such as low CD4+ T lymphocyte levels. In still other embodiments, the methods may be used in subjects who are HIV-positive and who may be immunocompromised, provided that the agent is administered in an amount, a dosing regimen, and an administration schedule that have a therapeutic effect on abnormal proliferation, such as in a Kaposi's sarcoma tumor, but are not therapeutically effective in stimulating hemopoiesis in the subject.

According to still other embodiments, subjects of the invention are those who may have previously received anti-cancer therapy or who will in the future receive anti-cancer therapy but who do not at the time of treatment need hemopoietic stimulation, including a blood transfusion or administration of a hemopoietic stimulant such as a hemopoietic growth factor.

Thus in certain embodiments, the subjects are not myeloid or lymphoid suppressed or are not candidates for treatment with an agent which causes such suppression at the time of treatment with the methods of the instant invention. Myeloid suppressing conditions are those which induce a reduction in myeloid cells such as erythrocytes, neutrophils or platelets, to below protective or normal levels. Exemplary myelosuppressed conditions are hemopoietic malignancies, including leukemia and lymphoma and diseases such as chronic idiopathic neutropenia, cyclic neutropenia, anemia and thrombocytopenia. Similarly, lymphoid suppressing conditions are those which induce a reduction in lymphoid cells such as T lymphocytes. Suppression of lymphoid cells or some myeloid cells such as granulocytes is also referred to as immunosuppression since reduction in these cell types makes an individual susceptible to, inter alia, infection. Subjects may be exposed to myeloid, lymphoid or general immune suppressing conditions by the use of either immunosuppressant drugs such as cyclosporin or high dose chemotherapeutic compounds which affect dividing hemopoietic cells. Immuno-suppression may also arise as a result of treatment modalities such as total body irradiation or conditioning regimens prior to bone marrow transplantation. Viral infection, particularly as in the case of infection with human immunodeficiency virus (HIV), may also immunosuppress an individual. In some embodiments, subjects are those which have not been exposed and are not anticipated to be exposed to the above-mentioned conditions. In other embodiments, the instant invention aims to treat subjects who may have been myelosuppressed or immunosuppressed (e.g., by exposure to one or more of the above conditions), provided that at the time of treatment using the methods described herein, the subject has protective or normal levels of hemopoietic cells.

In still other embodiments, the invention aims to treat subjects who may exhibit symptoms calling for hemopoietic stimulation, provided that the agents are administered in doses, routes and schedules that would not result in hemopoietic stimulation, as explained below. In certain embodiments, the methods of the invention are not intended for use in the treatment of malignancies in HIV infected (i.e., HIV positive or HIV+) subjects who have below normal or below protective levels of hemopoietic cells, unless the agents are used under conditions, such as administration routes, doses or dosing schedules, that are therapeutically effective in treating abnormal cell proliferation, as described herein, and not effective in stimulating hemopoiesis. For example, in some embodiments, the agent may be administered once a day, or twice a day, or three or more times a day, for more than 7 days, more than 10 days, more than 14 days or more than 20 days in order to achieve, for example, sustained desired systemic levels. In other embodiments, the agent may be given at timed intervals, such as, for example, every two days, every three days, every four days, every week or every two weeks. In still further embodiments, the agent may be delivered intravenously and continuously, for example, or by injection, such as, in single bolus administrations.

According to another aspect of the invention, methods are provided for inhibiting angiogenesis in disorders having a pathology which requires angiogenesis. Angiogenesis is defined as the formation of new blood vessels. One subset of these disorders is conditions characterized by abnormal mammalian cell proliferation. Another subset is non-cancer conditions including diabetic retinopathy, neovascular glaucoma and psoriasis.

In preferred embodiments, the methods of the invention are aimed at inhibiting tumor angiogenesis. Tumor angiogenesis refers to the formation of new blood vessels in the vicinity or within a tumor mass. Solid tumor cancers require angiogenesis particularly for oxygen and nutrient supply. It has been previously shown that inhibition of angiogenesis in solid tumor can cause tumor regression in animal models. Thus in one aspect, the invention relates to a method for inhibiting angiogenesis by inhibiting the proliferation, migration or activation of endothelial cells and fibroblasts, provided this angiogenesis is unrelated to wound healing in response to injury, infection or inflammation.

Thus in certain embodiments, the methods of the invention are intended for the treatment of diseases and processes that are mediated by angiogenesis including, but not limited to, hemangioma, solid tumors, tumor metastasis, benign tumors, for example hemangiomas, acoustic neuromas, neurofibromas and trachomas, Osler-Webber Syndrome, telangiectasia, myocardial angiogenesis, angiofibroma, plaque neovascularization, coronary collaterals, ischemic limb angiogenesis, comneal diseases, rubiosis, neovascular glaucoma, diabetic retinopathy, retrolental fibroplasia, diabetic neovascularization, macular degeneration, keloids, ovulation, menstruation, and placentation.

The compositions and methods of the invention in certain instances may be useful for replacing existing surgical procedures or drug therapies, although in most instances the present invention is useful in improving the efficacy of existing therapies for treating such conditions. Accordingly combination therapy may be used to treat the subjects. For example, the agent may be administered to a subject in combination with another anti-proliferative (e.g., an anti-cancer) therapy. Suitable anti-cancer therapies include surgical procedures to remove the tumor mass, chemotherapy or localization radiation. The other anti-proliferative therapy may be administered before, concurrent with, or after treatment with the agent of the invention. There may also be a delay of several hours, days and in some instances weeks between the administration of the different treatments, such that the agent may be administered before or after the other treatment.

As an example, the agent may be administered in combination with surgery to remove an abnormal proliferative cell mass. As used herein, "in combination with surgery" means that the agent may be administered prior to, during or after the surgical procedure. Surgical methods for treating epithelial tumor conditions include intra-abdominal surgeries such as right or left hemicolectomy, sigmoid, subtotal or total colectomy and gastrectomy, radical or partial mastectomy, prostatectomy and hysterectomy. In these embodiments, the agent may be administered either by continuous infusion or in a single bolus. Administration during or immediately after surgery may include a lavage, soak or perfusion of the tumor excision site with a pharmaceutical preparation of the agent in a pharmaceutically acceptable carrier. In some embodiments, the agent is administered at the time of surgery as well as following surgery in order to inhibit the formation and development of metastatic lesions. The administration of the agent may continue for several hours, several days, several weeks, or in some instances, several months following a surgical procedure to remove a tumor mass.

The subjects can also be administered the agent in combination with non-surgical anti-proliferative (e.g., anti-cancer) drug therapy. In one embodiment, the agent may be administered in combination with an anti-cancer compound such as a cytostatic compound. A cytostatic compound is a compound (e.g., a nucleic acid, a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

Suitable anti-proliferative drugs or cytostatic compounds to be used in combination with the agents of the invention include anti-cancer drugs. Anti-cancer drugs are well known and include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene: Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estrarnustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; z7azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists;. raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizoftran.; sobuzoxane; sodium borocaptate; sodium phenylacetate; solverol; somatomedin binding protein; sonermin; sparfosic acid; spicamycin D; spiromustinc; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating compounds include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purpose of the invention include the antiproliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen I 125, Fludeoxyglucose F 18, Fluorodopa F 18, Insulin I 125, Insulin I 131, lobenguane I 123, lodipamide Sodium 1131, lodoantipyrine I 131, lodocholesterol I 131, lodohippurate Sodium I 123, Iodohippurate Sodium I 125, lodohippurate Sodium I 131, lodopyracet I 125, lodopyracet I 131, Iofetamine Hydrochloride I 123, lomethin I 125, lomethin I 131, lothalamate Sodium I 125, lothalamatc Sodium I 131, lotyrosine I 131, Liothyronine I 125, Liothyronine I 131, Merisoprol Acetate Hg 197, Mcrisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

According to the methods of the invention, the agents of Formula I may be administered prior to, concurrent with, or following the other anti-cancer compounds. The administration schedule may involve administering the different agents in an alternating fashion. In other embodiments, the agent may be delivered before and during, or during and after, or before and after treatment with other therapies. In some cases, the agent is administered more than 24 hours before the administration of the other anti-proliferative treatment. In other embodiments, more than one anti-proliferative therapy may be administered to a subject. For example, the subject may receive the agents of the invention, in combination with both surgery and at least one other anti-proliferative compound. Alternatively, the agent may be administered in combination with more than one ant-icancer drug.

Other compounds useful in combination therapies with the inhibitor compounds of the invention include anti-angiogenic compounds such as angiostatin, endostatin, fumagillin, non-glucocorticoid steroids and heparin or heparin fragments and antibodies to one or more angiogenic peptides such as αFGF, βFGF, VEGF, IL-8 and GM-CSF. These latter anti-angiogenic compounds may be administered along with the inhibitor agents of the invention (i.e., the agents of Formula I) for the purpose of inhibiting proliferation or inhibiting angiogenesis in all of the aforementioned conditions as described herein. In certain embodiments, the agent may be administered in combination with an anti-angiogenic compound and at least one of the anti-proliferative therapies described above including surgery or anti-proliferative drug therapy.

The above-described drug therapies are well known to those of ordinary skill in the art and are administered by modes known to those of skill in the art. The drug therapies are administered in amounts which are effective to achieve physiological goals such as the inhibition of proliferation or inhibition of angiogenesis, in combination with the agents of the invention. It is contemplated that the drug therapies may be administered in amounts which, when used alone, may not be capable of inhibiting proliferation or angiogenesis but which, when administered in combination with the agents of the invention, are capable of achieving the desired level of inhibition. Thus, in embodiments in which the agent of Formula I is administered with another therapeutic agent (e.g., an anti-proliferative compound or an anti-angiogenic compound), subtherapeutic doses of either or both agents may be used. In still other embodiments, anti-proliferative drug therapies may be administered in conditions such as doses or amounts which do not affect hemopoietic cell levels in the subjects.

The agents of the invention are administered in therapeutically effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

According to other aspects of the invention directed at inhibiting angiogenesis in a subject having a condition characterized by an abnormal mammalian cell proliferation, an effective amount to inhibit angiogenesis would be an amount sufficient to lessen or inhibit altogether smooth muscle cell proliferation so as to slow or halt the development of or the progression of tumor vascularization. As used in these embodiments, "inhibit" embraces all of the foregoing.

When used therapeutically, the agent is administered in therapeutically effective amounts. In general, a therapeutically effective amount means that amount necessary to delay the onset of, inhibit the progression of, or halt altogether the particular condition being treated. In some aspects of the invention, an therapeutically effective amount will be that amount necessary to inhibit mammalian cell proliferation. In other embodiments, a therapeutically effective amount will be an amount necessary to extend the dormancy of micrometastases or to stabilize any residual primary tumor cells following surgical or drug therapy.

In still other embodiments, the agent is delivered in an amount, a dose, and a schedule which is therapeutically effective in inhibiting proliferation yet which is not therapeutically effective in stimulating hemopoiesis in the subject. In administering the agents of the invention to subjects, dosing amounts, dosing schedules, routes of administration and the like can be selected so as to affect the other known activities of these compounds. For example, amounts, dosing schedules and routes of administration can be selected as described below, whereby therapeutically effective levels for inhibiting proliferation are provided, yet therapeutically effective levels for restoring hemopoietic deficiency are not provided. As another example, local administration to tumors or protected body areas such as the brain may result in therapeutically effective levels for inhibiting proliferation, but may be non-therapeutically effective levels for hemopoietic cell stimulation.

In addition, agents of Formula I can be selected that are effective as anti-proliferative agents but are relatively ineffective as hemopoietic cell stimulatory or activating agents. Thus, certain subjects who require both hemopoietic stimulation and/or activation and proliferation inhibition may be treated with different agents of Formula I simultaneously, one each for the desired therapeutic effect, or with a single agent but in different dosages, schedules, and/or route to achieve both hemopoietic stimulation and proliferation inhibition at therapeutic levels.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. In some embodiments, the agents are administered for more than 7 days, more than 10 days, more than 14 days and more than 20 days. In still other embodiments, the agent is administered over a period of weeks, or months. In still other embodiments, the agent is delivered on alternate days. For example, the agent is delivered every two days, or every three days, or every four days, or every five days, or every six days, or every week, or every month.

The agents of the invention can also be administered in prophylactically effective amounts, particularly in subjects diagnosed with benign or pre-malignant tumors. In these instances, the agents are administered in an amount effective to prevent the development of an abnormal mammalian cell proliferative mass or to prevent angiogenesis in the solid tumor mass, depending on the embodiment. The agents may also be administered in an amount effective to prevent metastasis of cells from a tumor to other tissues in the body. In these latter embodiments, the invention is directed to preventing the metastatic spread of a primary tumor.

According to another aspect of the invention, a kit is provided. The kit is a package which houses a container which contains an agent of the invention and also houses instructions for administering the agent of the invention to a subject having a condition characterized by an abnormal mammalian cell proliferation. The kit may optionally also contain one or more other anti-proliferative compounds or one or more anti-angiogenic compounds for use in combination therapies as described herein.

In still another aspect of the invention, kits for administration of an agent of the invention to a subject is provided. The kits include a container containing a composition which includes at least one agent of the invention, and instructions for administering the at least one agent to a subject having a condition characterized by an abnormal mammalian cell proliferation in an amount effective to inhibit proliferation. In certain embodiments, the container is a container for intravenous administration. In other embodiments the agent is provided in an inhaler. In still other embodiments, the agent is provided in a polymeric matrix or in the form of a liposome. In yet other embodiments, kits are provided for the administration of an agent of the invention to a subject having an abnormal mammalian cell mass for the purpose of inhibiting angiogenesis in the cell mass. In these latter kits, the agent is provided in an amount effective to inhibit angiogenesis along with instructions for use in subjects in need of such treatment.

The agent may be administered alone or in combination with the above-described drug therapies by a variety of administration routes available. The particular mode selected will depend, of course, upon the agent selected, the condition being treated, the severity of the condition, whether the treatment is therapeutic or prophylactic, and the dosage required for efficacy. The methods of the invention, generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

When using the agent of the invention in subjects in whom the primary site of abnormal proliferation is well delineated and easily accessible, direct administration to the site may be preferred, provided the tumor has not already metastasized. For example, administration by inhalation for lung tumors or by suppositories in the treatment of cervical, ovarian or rectal tumors may be preferred. Likewise, melanoma, for example, may be treated with the agent via topical administration in and around the area of the lesion. In still other embodiments aimed at the treatment of subjects with breast or prostate cancer, the agents may be delivered by injection directly into the tissue with, for example, a biopsy needle and syringe.

Systemic administration may be preferred in some instances such as, for example, if the subject is known to have or is suspected of having metastases. In this way, all tumor sites, whether primary or secondary may receive the agent Systemic delivery may be accomplished through for example, oral or parenteral administration. Inhalation may be used in either systemic or local delivery, as described below.

As discussed earlier, the agent may also be delivered to a tumor site during or immediately after a surgical procedure to remove the tumor by lavage into the excision site or by perfusion of the affected tissue with a physiologically acceptable solution containing the agent. Alternatively, the patient may be administered the agent prior to or following the surgical procedure by continuous infusion. In yet other embodiments, a sustained release device, as described below, such as a polymeric implant may be positioned during surgery in the vicinity of the excision site so as to provide a high local concentration of the agent. These latter embodiments may be appropriate to prevent regrowth of the tumor.

The agent of the invention may be administered alone or in combination with the above-described drug therapies as part of a pharmaceutical composition. Such a pharmaceutical composition may include the agent in combination with any standard physiologically and/or pharmaceutically acceptable carriers which are known in the art. The compositions should be sterile and contain either a therapeutically or prophylactically effective amount of the agent in a unit of weight or volume suitable for administration to a subject. The term "pharmaceutically-acceptable carrier" as used herein means one or more compatible solid or liquid filler, diluents or encapsulating substances which are suitable for administration into a subject of the invention. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically-acceptable further means a non-toxic material that is compatible with a biological system such as a cell, cell culture, tissue, or organism. The characteristics of the carrier will depend on the route of administration. Physiologically and pharmaceutically-acceptable carriers include diluents, fillers, salts, buffers, stabilizers, solubilizers, and other materials which are well known in the art.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(drtho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly (isopropyl acrylate), poly(isobutyl acrylate), and poly(octadecyl acrylate). Thus, the invention provides a composition of the above-described agents of Formula I for use as a medicament, methods for preparing the medicament and methods for the sustained release of the medicament in vivo.

Other delivery systems can include timed release, delayed release or sustained release delivery systems. Such systems can avoid repeated administrations of the agent of the invention, increasing convenience to the subject and the physician, Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions, such as a the suspected presence of dormant metastases. Long-term release, are used herein, means that the implant is constructed and arranged to delivery therapeutic levels of the active ingredient for at least 30 days, at least 60 days and more preferably for several months. Long-term sustained release implants are well-known to those of ordinary skill in the art and include some of the release systems described above.

In still other embodiments, the agent is targeted to a site of abnormal cell proliferation, such as, a tumor, through the use of a targeting compound specific for a particular tissue or tumor type. The agents of the invention may be targeted to primary or in some instances, secondary (i.e., metastatic) lesions through the use of targeting compounds which preferentially recognize a cell surface marker. The targeting compound may be directly conjugated to the agents of the invention via a covalent linkage. The agent may be indirectly conjugated to a targeting compound via a linker. Alternatively, the targeting compound may be conjugated or associated with an intermediary compound such as, for example, a liposome within which the agent is encapsulated. Liposomes are artificial membrane vessels which are useful as a delivery vector in vivo or in vitro. It has been shown that large unilamellar vessels (LUV), which range in size from 0.2–4.0 μm can encapsulate large macromolecules. Liposomes may be targeted to a particular tissue, such as the vascular cell wall, by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985). In still other embodiments, the targeting compound may be loosely associated with the agents of the invention, such as within a microparticle comprising a polymer, the agent of the invention and the targeting compound.

Targeting compounds useful according to the methods of the invention are those which direct the agent to a site of abnormal proliferation such as a tumor site. The targeting compound of choice will depend upon the nature of the tumor or the tissue origin of the metastasis. In some instances it may be desirable to target the agent to the tissue in which the tumor is located. For example, agents can be delivered to breast epithelium by using a targeting compound specific for breast tissue. In preferred embodiments, the target is specific for malignant breast epithelium. Examples of compounds which may localize to malignant breast epithelium include, but are not limited to, estrogen and progesterone, epithelial growth factor (EGF) and HER-2/neu ligand, among others. The HER-2/neu ligand may also be used to target agents to ovarian cancers. Ovarian cancers are also known to express EGFR and c-fms, and thus could be targeted through the use of ligands for either receptor. In the case of c-fms which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of *E. Coli*; in breast epithelium: heregulin, prolactin, transferrin, cadherin-11. Other markers specific to particular tissues are available and would be known to one of ordinary skill in the art.

In still other embodiments, the agent of the invention may be targeted to fibroblasts specifically, via ligands or binding partners for fibroblast specific markers. Examples of these markers include, but are not limited to fibroblast growth factors (FGF) and platelet derived growth factor (PDGF). In some embodiments, it may be desirable to target the agent to FAP-α specifically through the use of binding peptides for FAP-α which do not interfere with inhibition by the agent of the invention. One such binding peptide is the monoclonal antibody F19, used previously for immunodetection of reactive stromal fibroblast expressing FAP-α.

Agents useful in the invention can be identified using a screening assay method for determining whether a putative agent is able to inhibit the activity of FAP-α, thereby inhibiting cell proliferation. The initial screening assay can be conducted in an in vitro system with a readout of FAP-α inhibition. In such screening assays; cells expressing FAP-α but not CD26 can be used as a source of FAP-α.

Alternatively, recombinant or purified FAP-α can also be used in either a soluble or bound form. The choice of whether to use FAP-α in either a soluble or bound form may depend upon the source of the compounds to be screened. For example, if the compounds to be screened are present in phage libraries, it may be desirable to use soluble FAP-α. If, on the other hand, the compounds are synthesized by combinatorial chemistry techniques, then bound FAP-α may be more suitable. It is possible to immobilize FAP-α in 96 well plates through either direct binding to the surface, or more preferably through the indirect binding via an anti-FAP-α antibody or antibody fragment such as that derived from F19, a FAP-α specific antibody. Binding is achieved through incubation at room temperature for 2 hours, followed by washing with a phosphate buffered saline solution containing a suitable non-specific blocking agent such as albumin or serum. After significant washing, the substrate alanylprolyl-7-amido-4-trifluoromethyl-coumarin (Ala-Pro-NH-F3-Mec, available from Bachem) is added to the plates and incubated for 1 hour at 37° C. in 100 mM Tris/HCl, pH7.8, 100 mM NaCl. At the end of the incubation, a fluorometric measurement is made for each well using an excitation wavelength of 390 nm and an emission wavelength of 538 nm. The substrate described above can also be used in soluble FAP-α enzyme inhibition assays are described in U.S. Patent Application entitled "Multivalent Compounds for Crosslinking Receptors and Uses Thereof" filed on Apr. 12, 1999 and assigned U.S. Ser. No. 09/290,376 (pending).

The above described procedure represents the control for the inhibition screen. To perform the inhibition screen, the agents of Formula I are incubated with FAP-α for 5–10 minutes at 37° C. prior to introduction of the substrate. The enzyme reaction proceeds as above, and a fluorescent measurement is used as a readout. A decrease in the amount of fluorescence is indicative of an inhibitor. Alternatively, the readout can be a kinetic analysis of the rate of fluorescence change, with a slower rate being indicative of an inhibitory agent.

Once FAP-α inhibitors have been pre-screened in vitro, they can be tested in proliferation assays in vitro or in vivo. In vitro proliferation assays could analyze the effect of Formula I compounds on the rate of proliferation of FAP-α expressing cells. Proliferation in these assays can be measured either by tritiated thymidine uptake or simply by a cell count. Carcinoma cell lines are not suitable for these types of in vitro assays since these cells are generally FAP-α negative. Alternatively, inhibition of FAP-α protease activity in vitro or in vivo or inhibition of angiogenesis in vitro could also be used. Assay systems for angiogenesis inhibition are known in the art and are described in U.S. Pat. Nos. 5,854,221 and 5,639,725, the entire contents of which are incorporated herein by reference. In vivo assay systems involve the initial induction of a suitable experimental tumor within a mouse, usually by the injection of a malignant cell line into a pre-defined location such as the lungs or the footpad. Following the implantation and growth of the tumor, the agent to be tested is administered to the mouse, again usually over a period of time, and at differing doses. At the end of the assay, the mouse is analyzed in terms of, among other things, tumor growth and the presence of metastases. In assay systems aimed at studying the prophylactic efficacy of an agent, the agent may be administered in close temporal proximity to the tumor cell line injection. In this way, one can determine whether the agent is able to prevent tumor formation altogether. These assay systems are described in more detail in the following Examples.

Identifying compounds and administration regimens which favor proliferation inhibition over hemopoietic stimulation, including dosing amounts, dosing schedules and routes of administration, involves comparison of results of the above assays to hemopoietic stimulation assays described previously in U.S. patent application Ser. No. 09/304,199, filed May 3, 1999, entitled "Hematopoietic Stimulation", now issued as U.S. Pat. No. 6,300,314, issued Oct. 9, 2001, the contents of which are incorporated herein in their entirety by reference.

The invention will be more fully understood by reference to the following examples. These examples, however, are merely intended to illustrate the embodiments of the invention and are not to be construed to limit the scope of the invention.

All patents, patent applications, references and other documents identified herein are incorporated in their entirety herein by reference.

EXAMPLES

Example 1

This example illustrates the use of PT-100 (i.e., ValboroPro) to inhibit FAP-α protease activity and stromal cytokine secretion from FAP-α positive CD26/DPPIV negative rat and human stromal cells.

Materials and Methods:

Rat Stromal Cultures

Cell Source. 8–12 week old female wild type CD26 positive ($D^+$) and CD26 negative ($D^-$) Fischer rat (Charles River Labs, Japan) bone marrow.

Bone marrow Preparation. Bone marrow was flushed from each femur, tibia and fibula with Dulbecco's phosphate buffered saline (D-PBS) using a 21-gauge needle and a 10 ml syringe. After removal, the bone marrow was immediately aspirated through the needle to make a single cell suspension. The cells were washed twice with sterile PBS and resuspended in MyeloCult H5100 long-term culture (LTC) media, available from Stem Cell Technologies, and supplemented with freshly diluted $10^{-6}$ M hydrocortisone, available from Sigma.

Establishment of adherent bone marrow stromal cell cultures. $1-2 \times 10^7$ cells were seeded into a T25 flask (Corning) containing 10 mls of LTC medium and incubated at 37° C. in 100% humidified 5% $CO_2$ in air. After 1 week half the medium was exchanged for fresh medium and incubated for approximately 1 week until a confluent cell layer formed.

PT-100 incubation. The adherent stromal cells were removed from the flask by trypsin-EDTA (Life Technologies, Inc.) digestion, washed once with sterile PBS and resuspended in long term culture medium at $1 \times 10^5$/ml. One ml of cells was seeded in each well of a 12-well tissue culture treated plate. PT-100 was diluted in medium and added immediately to the stromal cells at the appropriate concentrations ($10^{-1}$ to $10^{-8}$ M) and the cultures were incubated at 37° C. in 100% humidified 5% $CO_2$ in air.

Supernatant collection. The supernatants were collected from the stromal cultures after 1 or 2 days of incubation and either assayed immediately or stored at −20° C.

ELISA. The supernatants were assayed for IL-6 production using a commercially available ELISA kit (Biosource International).

DPPIV-like activity assay. Following the removal of supernatant from the stromal cultures, the adherent cells were washed with D-PBS and assayed for DPPIV-like activity. The fluorogenic substrate Ala-Pro-AFC was diluted in DPPIV buffer (50 mM Hepes, 140 mM NaCl) from the original stock of 10 mM (stored at −20° C. as a solution in dimethyl-formamide) to 1 mM, directly before the assay. 30

μl of the 1 mM stock was added per ml of buffer and the stromal cells were incubated for 10 minutes with 1 ml per well of the diluted substrate. The reaction was stopped by removing the substrate solution from each well and measured in the fluorescence spectrophotometer or stored −20° C. Activity was measured using an excitation wavelength of 400 nm and emission wavelength of 505 nm.

Human Stromal Cultures

Cell source. Bone marrow was kindly donated by New England Medical Center, Boston, Mass. and Dr. Richard Benjamin from Brigham and Women's Hospital in Boston, Mass. Mononuclear cells were purified over Ficoll and used immediately or frozen in liquid nitrogen.

Establishment of human stromal feeder layer. 2 to $4 \times 10^7$ human bone marrow mononuclear cells were seeded into a T75 flask (Corning) containing 20 mls of LTC medium and incubated at 37° C. in 100% humidified 5% $CO_2$ in air. After 1 week half the medium was exchanged for fresh medium and incubated for approximately 1 week when a confluent cell layer formed.

MyeloCult H5100 long-term culture (LTC) media can be obtained from Stem Cell Technologies and contains 12.5% horse serum, 12.5% fetal bovine serum, 0.2 mM I-inositol, 20 mM folic acid, $10^{-1}$2-β-mercapto-ethanol, 2 mM L-glutamine inα-MEM. Prior to using, add freshly diluted $10^{-6}$ M hydrocortisone, available from Sigma.

ELISA of human cells. Cultured supernatants were assayed for a high sensitivity ELISA (R+D Systems).

Human cell surface staining. The phenotype of the established human bone marrow stromal cells as determined using immunofluorescent staining with monoclonal antibodies specific for CD26 and FAP alpha, followed by fluorescence activated cell sorting (FACscan, Becton Dickinson). FAP alpha was stained using a biotinylated monoclonal anti-human antibody (IgG1 isotype) followed by Strepavidin-Fluorescein Isothiocyanin (SA-FITC). The antibody was purified over protein G, using cultured supernatants from the hybridoma F19 (ATCC), and biotinylated using biotinyl-p-nitrophenyl ester (Sigma). CD26 was stained with Cy-chrome or Phycoerythrin anti-human CD26 (clone MA261). Mouse IgG1 (Pharmigen) was used for a negative control.

PT-100 incubation, supernatant collection and DPPIV-like activity assay for human and rat cells were carried out in an identical manner.

Results

Table 1 shows three representative experiments which demonstrate normal DPPIV-like activity on rat bone marrow stromal cells which lack CD26. The DPPIV-like activity is potently inhibited by PT-100. Bone marrow stromal cells were established from the long bones of Fischer $D^+$ and $D^-$ rats and cultured for 2 days in the presence or absence of PT-100. Cells were assayed for DPPIV-like activity as described in the Materials and Methods section. DPPIV-like activity is presented as velocity and the percent of protease activity inhibition with PT-100 is calculated relative to a 'no treatment' control.

TABLE 1

Comparison of DPPIV-Like Activity of Fischer $D^+$ and $D^-$ Rat BM Stromal Cells

| Experiment # | Rat Phenotype | DPPIV-Like Activity (Velocity = pMoles/min) | % Inhibition by $10^{-6}$ MPT-100 |
|---|---|---|---|
| 102098 | $D^+$ | 23.4 | 76.9 |
|  | $D^-$ | 23.3 | 62.1 |
| 102198 | $D^+$ | 22.4 | 35.5 |
|  | $D^-$ | 33.7 | 86.4 |
| 102398 | $D^-$ | 35.8 | 73.8 |

Figure 1B:
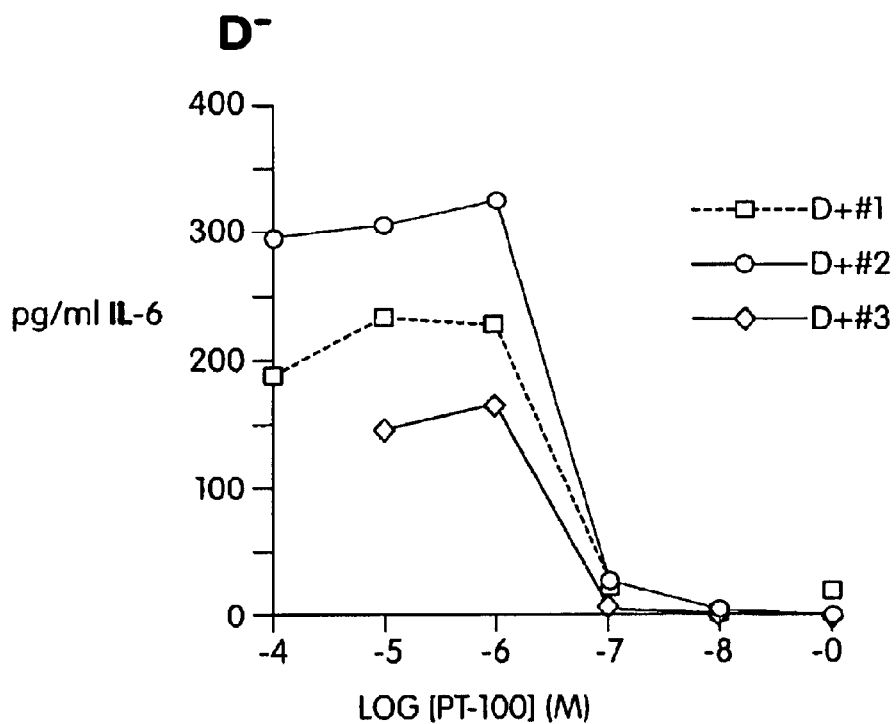
FIG. 1b is a comparison of response of Fischer $D^-$ rat and BM stromal cells to PT-100 in vitro by measurement of interleukin-1 (IL-6) release.
Figure 2A:
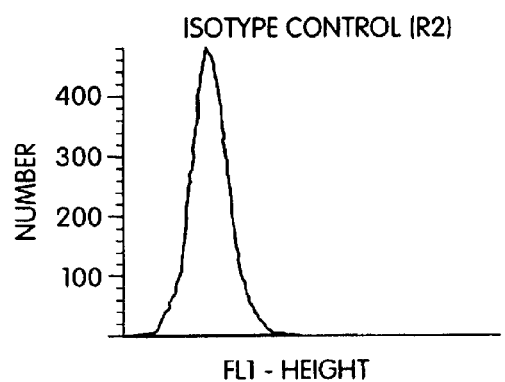
FIG. 2A is a profile of isotype control cell surface expression by human bone marrow stromal cells.
Figure 2B:
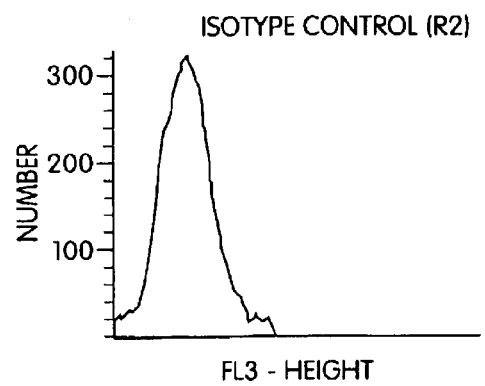
FIG. 2B is a profile of isotype control cell surface expression by human bone marrow stromal cells.
Figure 2C:
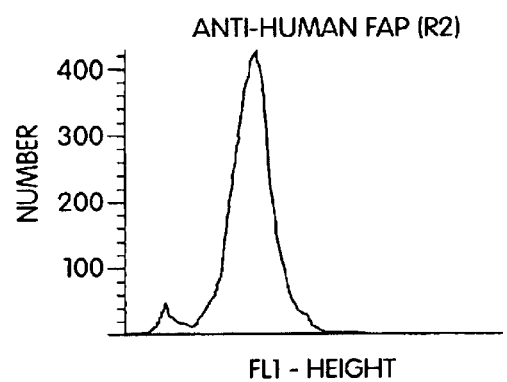
FIG. 2C is a profile of FAP-α cell surface expression by human bone marrow stromal cells.
Figure 2D:
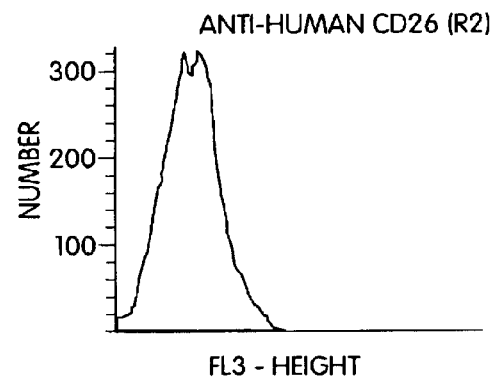
FIG. 2D is a profile of CD26 cell surface expression by human bone marrow stromal cells.

FIG. 1 shows the comparison of the response of Fischer $D^+$ and $D^-$ rat and bone marrow stromal cells to PT-100 in in vitro cultures. Similar levels of IL-6 are secreted from bone marrow stromal cells of $D_+$ and $D^-$ rats. Moreover, IL-6 levels for both strains were enhanced by the addition of PT-100. Bone marrow stromal cells were established from the long bones of 3 Fischer $D_+$ and $D^-$ rats as described in Materials and Methods. The stromal cells were incubated for 2 days in the presence or absence of the indicated concentrations of PT-100. IL-6 levels in the culture supernatant were determined by ELISA.

A fluorescent activated cell sorting (FACS) profile of human bone marrow stromal cells is shown in FIG. 2. Human stromal cells can be established which lack cell surface CD26 but express the DPPIV-like protein FAP-α. Stromal cells were established from the bone marrow of a human volunteer as described in Materials and Methods. Cultured cells were removed by trypsin digestion and assayed for surface expression of CD26 and FAP-α by immuno-fluorescence staining and cell sorting. The FACS profile for FAP-α (FL1) and CD26 (FL2) are represented as histograms. Negative controls used in this experiment were biotinylated mouse IgG1/SA-FITC and Cychrome-mouse IgG1 (top panels). FAP alpha was stained with biotinylated F19 followed by secondary staining with SA-FITC. CD26 was stained with PE-mouse anti-human CD26.

Figure 3A:
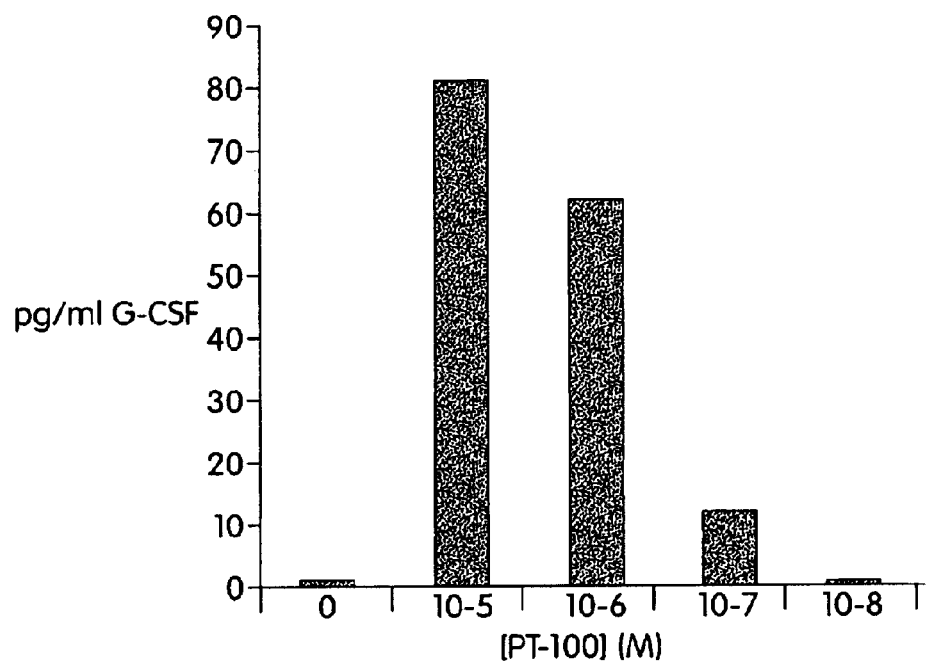
FIG. 3a is the PT-100 dose response of FAP-$α^+$ CD26$^-$ primary human stromal cells by measurement of granulocyte-colony stimulating factor (G-CSF) release.
Figure 3B:
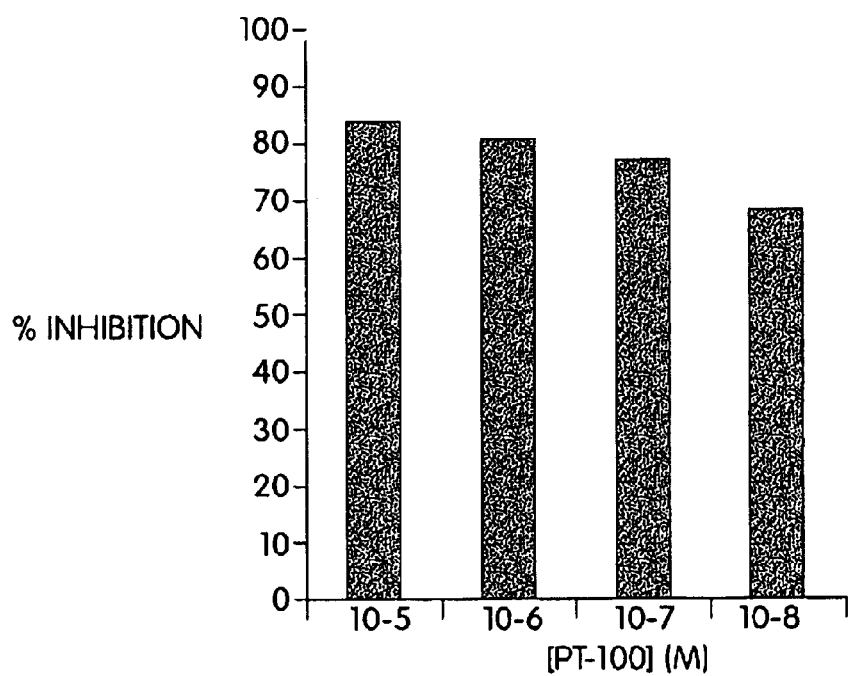
FIG. 3b is the PT-100 dose response of FAP-$α_+$ CD26$^-$ primary human stromal cells by measurement of inhibition of DPPIV-like activity.

FIG. 3 demonstrates that primary human stromal cells which express FAP, but not CD26, respond to PT-100. Human bone marrow cells that lack CD26 but express FAP-α, as determined by FACS analysis, were potently stimulated by PT-100 to release G-CSF. The DPPIV-like activity associated with the intact cells was inhibited by PT-100. Stromal cells were established from the bone marrow of a human volunteer as described in the materials and methods. The stromal cells were incubated for 2 days in the presence or absence of the indicated concentrations of PT-100 and cultured supernatants were assayed for IL-6 or DPPIV-like activity as described in Materials and Methods.

Example 2

This example illustrates the anti-tumor activity of PT-100 (i.e., Val-boro-Pro) in mouse models.

PT-100 administered orally significantly inhibits the growth of both the B16 melanoma and the WEHI-164 fibrosarcoma in mice.

Figure 4:
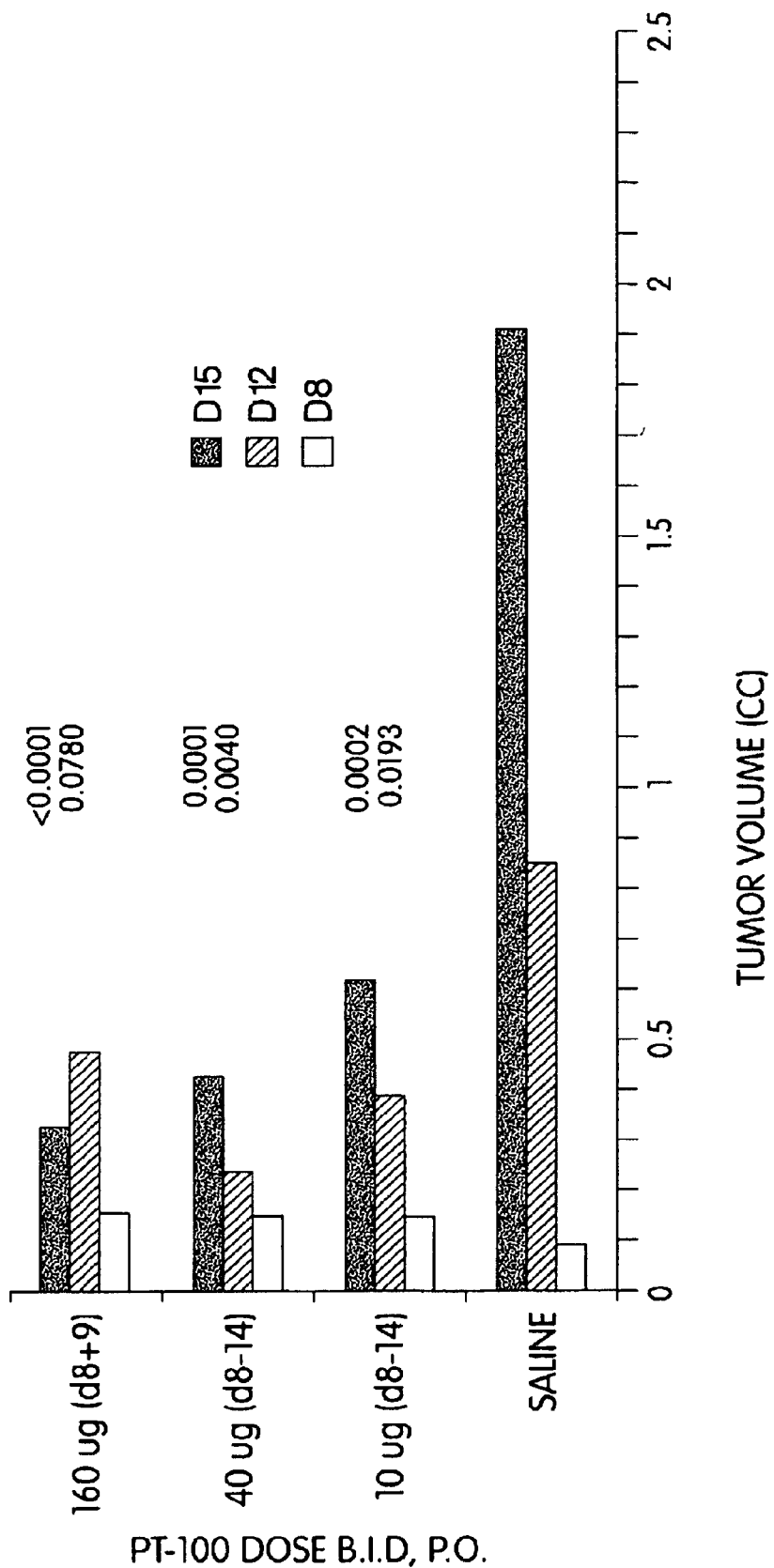
FIG. 4 is a bar graph showing the effect of PT-100 treatment on established subcutaneous B16-F10 tumors.

The highly metastatic B16-F0 tumor was implanted subcutaneously (s.c.) in C57BL/6 mice. PT-100 administration was started on day 8 when palpable tumors were apparent. Tumor volumes were measured on days 8, 12, and 15. The data are shown in FIG. 4. In mice treated with doses of 10 and 40 μg of PT-100 administered orally (p.o.), twice daily (b.i.d.) from day 8 to 14, tumor growth was markedly inhibited compared with the saline treated control mice. A higher dose of 160 μg PT-100 administered for just two days—day 8 and day 9—was also effective in suppressing tumor growth. In the experiment of FIG. 4 each experimental group contained 10 animals.

Figure 5A:
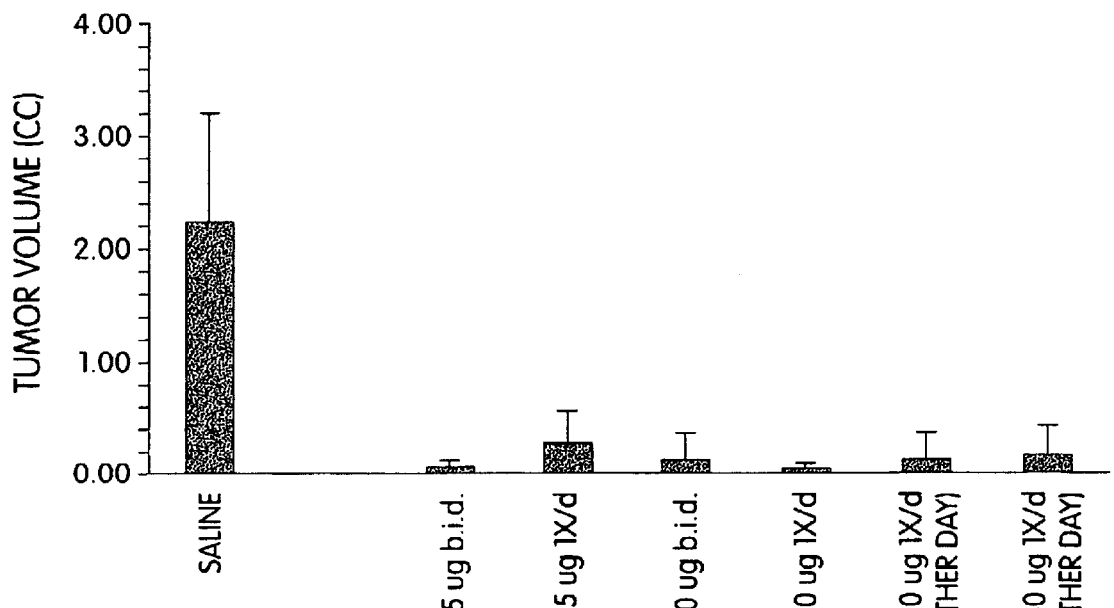
FIG. 5a is a bar graph showing the effect of PT-100 on WEHI subcutaneous growth (in terms of tumor volume) in vivo on day 20 post injection.
Figure 5B:
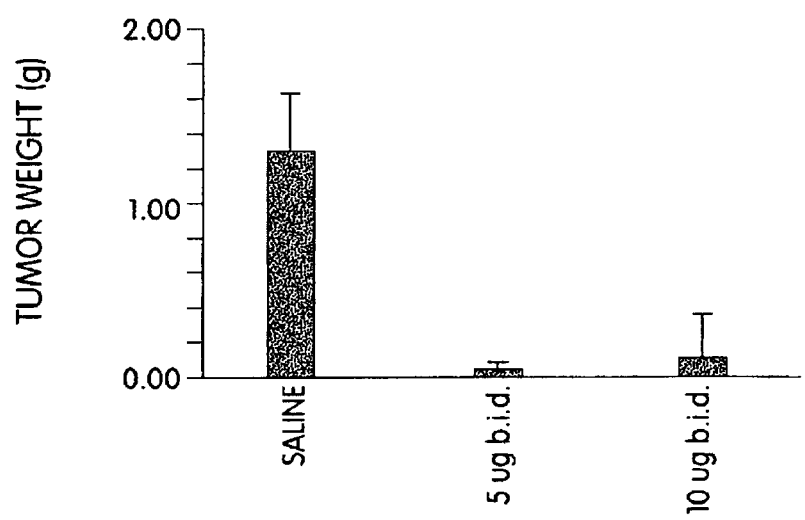
FIG. 5b is a bar graph showing the effect of PT-100 on WEHI subcutaneous growth (in terms of tumor weight) in vivo on day 20 post injection.

Similar experiments with the WEHI-164 fibrosarcoma demonstrated that PT-100 could suppress the growth of an established s.c. tumor. In addition, when PT-100 administration was started shortly after implantation of WEHI-164 on day 2, it was found that not only was tumor growth inhibited, but a proportion of the tumors also became necrotic and apparently regressed completely. Thus in the experiment of FIG. 5, the large reductions in tumor volume recorded were in part due to the absence of a palpable tumor in some of the mice in each of the PT-100 treated groups (10 replicate animals per group). For example, in the mice treated with the 5 μg dose of PT-100 administered b.i.d., 6 of the animals were completely free of a detectable s.c. tumor. PT-100 treatment of the mice in the experimental groups was stopped on day 20, the day when the data of FIG. 5 were recorded. These mice have now been monitored up to day 30 after WEHI-164 implantation, and to date, none of the mice recorded as tumor-free on day 20 has developed a detectable s.c. tumor.

Example 3

The in vivo effects of the compounds of the invention can be assayed through various animal models known to those of ordinary skill in the art. Generally such assays involve the injection of a carcinoma cell line, of mouse or preferably, human, origin, into a cohort of mice. Following the passage of several days, as determined by the proliferative rate of the cell line, parameters such as tumor size, degree of metastasis and cellular infiltration into a region in the vicinity of the tumor site are evaluated. In most experiments, two groups of experimental mice are studied: a first, control, group which receives only the cell line but no agent of Formula I, and a second, test, group which receives at least one agent of Formula I such as PT-100. This second group is divided into several subgroups each of which receives a different dose of the agent, preferably between 10 μg and 100 μg per day for 10–20 days. On these days, the control group will be administered control doses containing only vehicle with no active agent. The evaluation of tumor growth and organ specific metastasis will vary according to the tumor type studied.

In yet other assay systems aimed at determining the effect of the agents on metastatic spread or development, the agents are administered at the time of innoculation of the malignant cells or short thereafter. Similarly, the agents may be administered after the innoculation, but before the full development of the tumor mass. In these ways, the effects of agents on different stages of malignant growth and metastasis can be tested.

The following are examples of different in vivo model systems for studied a variety of epithelial cancers.

Lung carcinoma: One such example for lung carcinoma involves the subcutaneous flank injection of the M109 mouse lung tumor cell line into syngeneic mice. On each of days 4 through 8 after injection of the cell line, the mice receive single bolus daily doses of the compounds of the invention by tail vein injection. The compounds of the invention are prepared and administered in a carrier solution which is physiologically compatible with both the recipient environment and the stability of the compound. A preferable carrier solution is D-PBS with a carrier protein such as albumin. Mice are sacrificed at day 4 after cell line injection and at two day intervals after the administration of inhibitory compounds. The tumors are excised and weighed. Measurement data can be standardized relative to initial body weight of the recipient mouse.

Alternatively, if the transplantable tumor line is able to grow to the extent that it causes a reproducible and significant effect on total mouse body weight, than the recipients need not be sacrificed. In this readout system, starting at day 0 (i.e., prior to the introduction of the cell line), the mice are weighed daily to determine the tumor burden and to evaluate the effect of the injected compound(s) on tumor burden. Tumor mass can be calculated by the difference in mouse body mass during the experiment and at day 0. Measurement of control mice which receive only carrier solution with carrier protein will At be used to standardize for any unrelated weight gain.

Colon carcinoma: The effect of test agents on experimentally induced human colorectal tumors in mice can be deduced by transplanting into nude mice human colon tumor cell lines such as COLO 205, C-1H, 26M3.1, CT-26, LS174T, and HT29, in a manner similar to that described above. In these models, pericecal tumor growth, angiogenesis, ascites and metastasis to the liver are suitable readouts to ascertain if the test compounds are active.

Melanoma and metastatic melanoma: Melanoma cell lines (e.g., B16 and SKMEL) are administered either intraperitoneally or intravenously or directly into the footpad. Primary tumor growth, survival time, resistance to tumor challenge, cellular infiltrates characteristic of melanoma tumors, and extent of tumor angiogenesis are all parameters of interest which can be evaluated. In certain models of melanoma, metastasis to the lung can be readily observed following surgical removal of the primary tumor.

Ovarian cancer: Human ovarian carcinoma cell lines such as JAM are administered subcutaneously to severe combined immunodeficiency (SCID) mice. After 21 days, tumor growth is generally established and the effects of the test agent after this point can be compared to vehicle-alone.

Breast cancer: Breast cancer cell lines such as MDA-MB-231 are injected preferably into the left cardiac ventricle of mice. Many breast cancers metastasize to bone. About 4 weeks after inoculation, tumors and bone metastases can be evaluated as can the effect of administration of the test agent.

Squamous cell carcinoma: Human basaloid squamous cell carcinoma cells or established tumor lines such as HTB-1 are administered either subcutaneously or submucosally into mice. After allowing a sufficient time for primary tumor growth, the mice are administered test or control preparations, and the effects of the test agent on the parameters described above are determined.

Other transplantable cell lines useful in these assays include, but are not limited to, human NCI-H522 lung tumor cell line (nude mice recipients), human SKOV3 cell line, and the M5076 cell line.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety herein by reference.

We claim:

1. A method for treating a subject having a condition characterized by an abnormal mammalian cell proliferation, comprising:

administering to a subject in need of such treatment, a compound selected from the group consisting of an anti-angiogenic compound and an anti-cancer compound, and an agent, in an amount effective to inhibit the proliferation, wherein the agent is a compound of Formula III

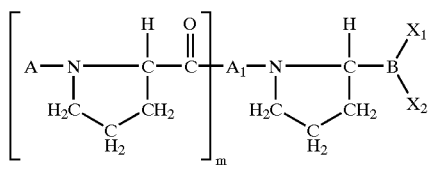

wherein m is an integer between 0 and 10, inclusive; A and $A_1$ are L- or D-amino acid residues; A in each repeating bracketed unit can be a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH.

2. The method of claim 1, wherein the abnormal mammalian cell proliferation is manifested as a tumor.

3. The method of claim 1, wherein the condition is further characterized by the presence of reactive stromal fibroblasts.

4. The method of claim 1, wherein the abnormal mammalian cell proliferation is in epithelial cells.

5. The method of claim 4, wherein the abnormal mammalian cell proliferation is selected from the group consisting of a carcinoma, a sarcoma, and a melanoma.

6. The method of claim 1, wherein the condition is a metastasis of epithelial origin.

7. The method of claim 1, wherein the condition is selected from the group consisting of breast cancer, colorectal cancer, ovarian cancer, prostate cancer, pancreatic cancer, kidney cancer, lung cancer, melanoma and fibrosarcoma.

8. The method of claim 1, wherein the condition is selected from the group consisting of bone and connective tissue sarcomas.

9. The method of claim 1, wherein the subject is otherwise free of symptoms calling for hemopoietic stimulation.

10. The method of claim 1, wherein the agent is administered in combination with surgery to remove an abnormal proliferative cell mass.

11. The method of claim 1, wherein the agent is administered to a patient who has had surgery to remove an abnormal proliferative cell mass.

12. The method of claim 1, wherein the agent is administered in combination with an anti-cancer compound.

13. The method of claim 1, wherein the agent is targeted to a tumor.

14. The method of claim 1, wherein the subject has normal hemopoietic activity.

15. The method of claim 1, wherein the subject is HIV negative.

16. The method of claim 1, wherein the agent is Val-boro-Pro.

17. A method for inhibiting angiogenesis in a subject having a condition characterized by abnormal mammalian cell proliferation comprising:

administering to a subject in need of such treatment, a compound selected from the group consisting of an anti-angiogenic compound and an anti-cancer compound, and an agent, in an amount effective to inhibit angiogenesis in an abnormal proliferative cell mass, wherein the agent is a compound of Formula III

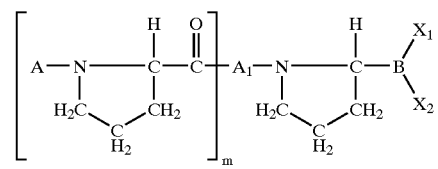

wherein m is an integer between 0 and 10, inclusive; A and $A_1$ are L- or D-amino acid residues; A in each repeating bracketed unit can be a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH.

18. The method of claim 17, wherein the agent is administered in combination with an anti-angiogenic compound.

19. A pharmaceutical preparation comprising:

an agent of Formula III

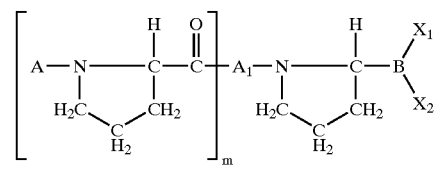

wherein m is an integer between 0 and 10, inclusive; A and $A_1$ are L- or D-amino acid residues; A in each repeating bracketed unit can be a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH, at least one other anti-cancer compound, and a pharmaceutically acceptable carrier.

20. A pharmaceutical preparation comprising:

an agent of Formula III

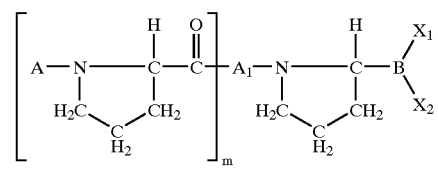

wherein m is an integer between 0 and 10, inclusive; A and $A_1$ are L- or D-amino acid residues; A in each repeating bracketed unit can be a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH, at least one other anti-angiogenic compound, and a pharmaceutically acceptable carrier.

21. A method for treating a subject having a condition characterized by an abnormal mammalian cell proliferation, comprising:

administering to a subject in need of such treatment, a compound selected from the group consisting of an anti-angiogenic compound and an anti-cancer compound, and an agent, in an amount effective to inhibit the proliferation, wherein the agent is a compound of Formula II

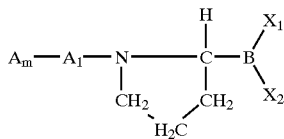

wherein m is an integer between 0 and 10, inclusive; A and $A_1$ are L- or D-amino acid residues; and each $X_1$ and $X_2$ is independently a hydroxyl group or a group capable of being hydrolyzed to a hydroxyl group in aqueous solution at physiological pH, and wherein the condition is further characterized by the presence of reactive stromal fibroblasts.

22. A method for treating a subject having a condition characterized by an abnormal mammalian cell proliferation, comprising:
administering to a subject in need of such treatment, a compound selected from the group consisting of an anti-angiogenic compound and an anti-cancer compound, and an agent, in an amount effective to inhibit the proliferation, wherein the agent is a compound of Formula II

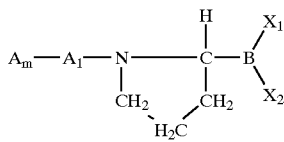

wherein m is an integer between 0 and 10, inclusive; A and $A_1$ are L- or D-amino acid residues; and each $X_1$ and $X_2$ is independently a hydroxyl group or a group capable of being hydrolyzed to a hydroxyl group in aqueous solution at physiological pH, and wherein the condition is selected from the group consisting of bone and connective tissue sarcomas.

23. The method of claim 1, wherein m in Formula III is zero.

24. The method of claim 23, wherein $A_1$ is selected from the group consisting of valine, lysine, proline and alanine.

25. The method of claim 1, wherein A and $A_1$ are L- or D-isomers of naturally occurring amino acid residues.

26. The method of claim 17, wherein m in Formula III is zero.

27. The method of claim 26, wherein $A_1$ is selected from the group consisting of valine, lysine, proline, and alanine.

28. The method of claim 17, wherein A and $A_1$ are L- or D-isomers of naturally occurring amino acid residues.

29. The pharmaceutical preparation of claim 19, wherein m in Formula III is zero.

30. The pharmaceutical preparation of claim 29, wherein $A_1$ is selected from the group consisting of valine, lysine, proline and alanine.

31. The pharmaceutical preparation of claim 19, wherein A and $A_1$ are L- or D- isomers of naturally occurring amino acid residues.

32. The pharmaceutical preparation of claim 20, wherein m in Formula III is zero.

33. The pharmaceutical preparation of claim 32, wherein $A_1$ is selected from the group consisting of valine, lysine, proline, and alanine.

34. The pharmaceutical preparation of claim 20, wherein A and $A_1$ are L- or D- isomers of naturally occurring amino acid residues.

35. The method of claim 12, wherein the anti-cancer compound is Aldesleukin, Asparaginase, Bleomycin Sulfate, Carboplatin, Chlorambucil, Cisplatin, Cladribine, Cyclophosphamide, Cytarabine, Dacarbazine, Dactinomycin, Daunorubicin hydrochloride, Docetaxel, Doxorubicin, Doxorubicin hydrochloride, Epirubicin hydrochloride, Etoposide, Etoposide phosphate, Floxuridine, Fludarabine, Fludarabine phosphate, Fluorouracil, Gemcitabine, Gemcitabine hydrochloride, Hydroxyurea, Idarubicin Hydrochloride, Ifosfamide, Interferons, Interferon-α2a. Interferon-α2b, Interferon-αn3, Interferon-γ1b, Interleukins, Irinotecan, Mechlorethamine hydrochloride, Melphalan, Mercatopurine, Methotrexate, Methotrexate sodium, Mitomycin, Mitoxantrone, Mitoxantrone hydrochloride, Paclitaxel, Pegaspargase, Pentostatin, Prednimustine, Porfimer sodium, Procarbazine Hydrochloride, Taxotere, Teniposide, Topotecan Hydrochloride, Vinblastine Sulfate, Vincristine Sulfate or Vinorelbine tartrate.

36. The method of claim 1, wherein the agent is administered in combination with an anti-angiogenic compound.

37. The method of claim 36, wherein the anti-angiogenic compound is angiostatin or endostatin.

38. The method of claim 18, wherein the anti-angiogenic compound is angiostatin or endostatin.

39. The pharmaceutical preparation of claim 19, wherein the anti-cancer compound is Aldesleukin, Asparaginase, Bleomycin Sulfate, Carboplatin, Chlorambucil, Cisplatin, Cladribine, Cyclophosphamide, Cytarabine, Dacarbazine, Dactinomycin, Daunorubicin hydrochloride, Docetaxel, Doxorubicin, Doxorubicin hydrochloride, Epirubicin hydrochloride, Etoposide, Etoposide phosphate, Floxuridine, Fludarabine, Fludarabine phosphate, Fluorouracil, Gemcitabine, Gemcitabine hydrochloride, lydroxyurea, Idarubicin Hydrochloride, Ifosfamide, Interferons, Interferon-a2a, Interferon-a2b, Interferon-αn3, Interferon-γ1b, Interleukins, Irinotecan, Mechlorethamine hydrochloride, Melphalan, Mercatopurine, Methotrexate, Methotrexate sodium, Mitomycin, Mitoxantrone, Mitoxantrone hydrochloride, Paclitaxel, Pegaspargase, Pentostatin, Prednimustine, Porfimer sodium, Procarbazine Hydrochloride, Taxotere, Teniposide, Topotecan Hydrochloride, Vinblastine Sulfate, Vincristine Sulfate or Vinorelbine tartrate.

40. The pharmaceutical preparation of claim 20, wherein the anti-angiogenic compound is angiostatin or endostatin.

41. The method of claim 21, wherein the agent is administered in combination with an anti-cancer compound.

42. The method of claim 41, wherein the anti-cancer compound is Aldesleukin, Asparaginase, Bleomycin Sulfate, Carboplatin, Chlorambucil, Cisplatin, Cladribine, Cyclophosphamide, Cytarabine, Dacarbazine, Dactinomycin, Daunorubicin hydrochloride, Docetaxel, Doxorubicin, Doxorubicin hydrochloride, Epirubicin hydrochloride, Etoposide, Etoposide phosphate, Floxuridine, Fludarabine, Fludarabine phosphate, Fluorouracil, Gemcitabine, Gemcitabine hydrochloride, Hydroxyurea, Idarubicin Hydrochloride, Ifosfamide, Interferons, Interferon-α2a, Interferon-α2b, Interferon-an3, Interferon-γ1b, Interleukins, Irinotecan, Mechlorethamine hydrochloride, Melphalan, Mercatopurine, Methotrexate, Methotrexate sodium, Mitomycin, Mitoxantrone, Mitoxantrone hydrochloride, Paclitaxel, Pegaspargase, Pentostatin, Prednimustine, Porfimer sodium, Procarbazine Hydrochloride, Taxotere, Teniposide, Topotecan Hydrochloride, Vinblastine Sulfate, Vincristine Sulfate or Vinorelbine tartrate.

43. The method of claim 21, wherein the agent is administered in combination with an anti-angiogenesis compound.

44. The method of claim 43, wherein the anti-angiogenic compound is angiostatin or endostatin.

45. The method of claim 22, wherein the agent is administered in combination with an anti-cancer compound.

46. The method of claim 45, wherein the anti-cancer compound is Aldesleukin, Asparaginase, Bleomycin Sulfate, Carboplatin, Chlorambucil, Cisplatin, Cladribine, Cyclophosphamide, Cytarabine, Dacarbazine, Dactinomycin, Daunorubicin hydrochloride, Docetaxel, Doxorubicin, Doxorubicin hydrochloride, Epirubicin hydrochloride, Etoposide, Etoposide phosphate, Floxuridine, Fludarabine, Fludarabine phosphate, Fluorouracil, Gemcitabine, Gemcitabine hydrochloride, Hydroxyurea, Idarubicin Hydrochloride, Ifosfamide, Interferons, Interferon-α2a, Interferon-α2b, Interferonα3, Interferon-γ1b, Interleukins, Irinotecan, Mechlorethamine hydrochloride, Melphalan, Mercatopurine, Methotrexate, Methotrexate sodium, Mitomycin, Mitoxantrone, Mitoxantrone hydrochloride, Paclitaxel, Pegaspargase, Pentostatin, Prednimustine, Porfimer sodium, Procarbazine Hydrochloride, Taxotere, Teniposide, Topotecan Hydrochloride, Vinblastine Sulfate, Vincristine Sulfate or Vinorelbine tartrate.

47. The method of claim 22, wherein the agent is administered in combination with an anti-angiogenesis compound.

48. The method of claim 47, wherein the anti-angiogenic compound is angiostatin or endostatin.

49. The method of claim 1, wherein the agent is administered locally.

50. The method of claim 1, wherein the agent is administered systemically.

51. The method of claim 17, wherein the abnormal mammalian cell proliferation is manifested as a tumor.

52. The method of claim 17, wherein the abnormal mammalian cell proliferation is in epithelial cells.

53. The method of claim 17, wherein the abnormal mammalian cell proliferation is selected from the group consisting of a carcinoma, a sarcoma, and a melanoma.

54. The method of claim 17, wherein the condition is a metastasis.

55. The method of claim 17, wherein the condition is selected from the group consisting of breast cancer, colorectal cancer, ovarian cancer, prostate cancer, pancreatic cancer, kidney cancer, lung cancer, melanoma and fibrosarcoma.

56. The method of claim 17, wherein the agent is administered locally.

57. The method of claim 17, wherein the agent is administered systemically.

58. The method of claim 17, wherein the subject is free of symptoms calling for hemopoietic stimulation.

59. The method of claim 17, wherein the agent is administered in combination with surgery to remove an abnormal proliferative cell mass.

60. The method of claim 17, wherein the agent is administered to a patient who has had surgery to remove an abnormal proliferative cell mass.

61. The method of claim 17, wherein the subject has normal hemopoietic activity.

62. The method of claim 17, wherein the subject is HIV negative.

63. The method of claim 17, wherein the agent is Val-boro-Pro.

64. The method of claim 17, wherein the agent is targeted to a tumor.

* * * * *

UNITED STATES PATENT AND TRADEMARK OFFICE
CERTIFICATE OF CORRECTION

PATENT NO. : 6,890,904 B1
DATED : May 10, 2005
INVENTOR(S) : Wallner et al.

It is certified that error appears in the above-identified patent and that said Letters Patent is hereby corrected as shown below:

Column 38,
Line 11, delete "." and insert -- , --.
Line 35, delete "lydroxyurea," and insert -- Hydroxyurea, --.
Line 36, delete "Interferon-a2a, Interferon-a2b," and insert -- Interferon-α2a, Interferon-α2b, --.
Line 59, delete Interferon-an3," and insert -- Interferon-αn3, --.

Column 39,
Line 17, delete "Interferonα3," and insert -- Interferon-αn3, --.

Signed and Sealed this

Nineteenth Day of July, 2005

JON W. DUDAS
*Director of the United States Patent and Trademark Office*